(12) United States Patent
Sala et al.

(10) Patent No.: US 8,952,222 B2
(45) Date of Patent: Feb. 10, 2015

(54) HERBICIDE RESISTANT SUNFLOWER PLANTS DERIVED FROM RW-B CULTIVAR

(75) Inventors: Carlos Sala, Venado Tuerto (AR); Mariano Bulos, Venado Tuerto (AR)

(73) Assignee: Anglo Netherlands Grain B.V., Rotterdam (NL)

( * ) Notice: Subject to any disclaimer, the term of this patent is extended or adjusted under 35 U.S.C. 154(b) by 833 days.

(21) Appl. No.: 13/056,237

(22) PCT Filed: Jul. 30, 2009

(86) PCT No.: PCT/NL2009/050468
§ 371 (c)(1),
(2), (4) Date: Apr. 27, 2011

(87) PCT Pub. No.: WO2010/014007
PCT Pub. Date: Feb. 4, 2010

(65) Prior Publication Data
US 2012/0058898 A1 Mar. 8, 2012

Related U.S. Application Data

(60) Provisional application No. 61/085,224, filed on Jul. 31, 2008.

(51) Int. Cl.
*A01H 1/00* (2006.01)
*A01H 5/00* (2006.01)
*C12N 15/82* (2006.01)
*A01H 5/10* (2006.01)
*C12N 9/10* (2006.01)

(52) U.S. Cl.
CPC .............. *C12N 15/8274* (2013.01); *A01H 5/10* (2013.01); *C12N 9/1022* (2013.01); *C12N 15/8278* (2013.01)
USPC ............ 800/300; 800/322; 800/295; 800/266

(58) Field of Classification Search
None
See application file for complete search history.

(56) References Cited

U.S. PATENT DOCUMENTS 7,807,882 B2 * 10/2010 Leon et al. .................... 800/300

FOREIGN PATENT DOCUMENTS

| EP | 1347056 | 9/2003 |
|---|---|---|
| WO | 2006024694 | 3/2006 |
| WO | WO 2007005581 A2 * | 1/2007 |
| WO | 2007/054555 | 5/2007 |

OTHER PUBLICATIONS

Tan et al, Imidazolinone-tolerant crops: history, current status and future, Pest Management Science (2005) 61:246-257.*
Helianthus annuus haplotype 1 acetohydroxyacid synthase 1 (AHAS1) gene sequence, GenBank Accession No. AU541451.1, Direct Submission, Submitted on Feb. 4, 2004.*
Jain S.M., Tissue culture-derived variation in crop improvement, Euphytica (2001) 118:153-166.*
International Search Report and Written Opinion for International Application No. PCT/NL2009/050468.
Database EPO Proteins "Sequence 24 from Patent WO2007054555," 1.eop.org/IBIS/exam/dbfetch.jsp?id=EPOP:CS642513, Jul. 19, 2007.
Tan et al., "Imidazolinone-tolerant crops: history, current status and future," Pest Management Science, vol. 61, 2005, pp. 246-257.
Miller et al., "Registrations of Germplasm," Crop Science, vol. 42, May-Jun. 2002, pp. 988-999.
Laureti et al., "Commercial Sunflower Hybrid Evaluation in East Central Italy," HELIA, vol. 30 No. 47, 2007, pp. 141-144.
Miller et al., "Utilization of Cross-Resistance to Create Herbicide-Resistant Sunflower Hybrids," Internet Article, URL:http://www.sunflowernsa.com/research/research-workshop/documents/136.pdf, Oct. 28, 2009, pp. 1 -5.
Gen Bank database Entry AAT07322.1; Oct. 29, 2002.

* cited by examiner

*Primary Examiner* — Cathy Kingdon Worley
*Assistant Examiner* — Mykola Kovalenko
(74) *Attorney, Agent, or Firm* — Lihua Zheng; Mary S. Consalvi; Proskauer Rose LLP

(57) ABSTRACT

Seeds and sunflower plants derived from cultivar RW-B and having increased resistance to herbicides relative to wild-type plants are provided. These plants contain a new genetic mutation in the AHAS gene which confers broad spectrum resistance to a combination of an imidazolinone, a sulfonylurea, a triazolopyrimidine, and a pyrimidinyloxybenzoate herbicide and mixtures thereof, including (i) resistance to cloransulam-methyl present in a concentration of at least 67 grams of active ingredient per hectare; and (ii) resistance to the mix of imazapyr present in a concentration of at least 160 grams per hectare and metsulfuron present in a concentration of at least 10 grams per hectare. RW-B is true breeding for the morphological traits of producing a plant with a single head, a yield of greater than one tonne per hectare and for producing a seed having an oil content of greater than 40%.

16 Claims, 8 Drawing Sheets

FIG. 1

```
AY541451    GAAAATCTGCCGGTTAAGATTTTATTACTTAACAACCAGCATTTGGGTATGGTGGTTCAGTGGGAGGA
B770        GAAAATCTGCCGGTTAAGATTTTATTACTTAACAACCAGCATTTGGGTATGGTGGTTCAGTGGGAGGA
RW-B        GAAAATCTGCCGGTTAAGATTTTATTACTTAACAATCAGCATTTGGGTATGGTGGTTCAGTTGGAGGA
U16280      GAAAATCTTCCTGTTAAGATTTTGTTACTTAACAATCAGCATTTGGGTATGGTGGTTCAGTGGGAGGA
AY124092    GAGCAACTTCCAGTGAAGATACTCTTATTAAACAACCAGCATCTTGGCATGGTTATGCAATGGGAAGA
                ^                                                            ^
            1660                                                         1721

AY541451    TCGGTTTTACAAGGCGAATCGGGCTCATACCTACTTAGGAAACCCGTCAAAAGAG
B770        TCGGTTTTACAAGGCGAATCGGGCTCATACCTACTTAGGAAACCCGTCAAAAGAG
RW-B        TCGGTTTTACAAGGCGAATCGGGCTCATACCTACTTAGGAAACCCGTCAAAAGAG
U16280      TCGGTTTTACAAGGCGAATCGGGCTCATACCTACTTAGGAAATCCGTCAAAAGAG
AY124092    TCGGTTTTACAAGGCTAACCGAGCTCACACATTTCTCGGGGATCCGGCTCAGGAG
```

FIG. 2

```
AY541451    ENLPVKILLLNNQHLGMVVQWEDRFYKANRAHTYLGNPSKE
B770        ENLPVKILLLNNQHLGMVVQWEDRFYKANRAHTYLGNPSKE
RW-B        ENLPVKILLLNNQHLGMVVQLEDRFYKANRAHTYLGNPSKE
U16280      ENLPVKILLLNNQHLGMVVQWEDRFYKANRAHTYLGNPSKE
AY124092    EQLPVKILLLNNQHLGMVMQWEDRFYKANRAHTFLGDPAQE
              ^                 ^
            554               574
```

FIG. 3

| Cross | F1 plants Number of plants scored | | | F2 populations Number of plants scored | | | Ratio tested | X2 p value | BC1F1 populations Number of plants scored | | | Ratio Tested | X2 p value |
|---|---|---|---|---|---|---|---|---|---|---|---|---|---|
| | R | I | S | R | I | S | | | R | I | S | | |
| HA89/RW-73 | 0 | 23 | 0 | 129 | 247 | 102 | 1:2:1 | 0.17 | 0 | 157 | 61 | 1:1 | 0.31 |
| B770/RW-73 | 0 | 31 | 0 | 152 | 305 | 165 | 1:2:1 | 0.68 | 0 | 317 | 97 | 1:1 | 0.46 |

FIG. 4

| | | Sulfonylureas | | | Imidazolinones | | | Pyrimidinyl-thiobenzoates | Triazolopyrimidines |
|---|---|---|---|---|---|---|---|---|---|
| Genotype | Mutation | foramsulfuron | chlorsulfuron | nicosulfuron | imazamox | imazapyr | imazapic | bispyribac-Na | cloransulam-methyl |
| | | 240 gr a.i./ha | 25 gr a.i./ha | 100 gr a.i./ha | 180 gr a.i./ha | 160 gr a.i./ha | 100 gr a.i./ha | 80 gr a.i./ha | 67 gr a.i./ha |
| B770 | WT | 9.0 c | 8.8 c | 9.0 b | 9.0 c | 9.0 c | 9.0 c | 9.0 d | 9.0 b |
| HA89 | WT | 8.7 c | 9.0 c | 9.0 b | 9.0 c | 9.0 c | 9.0 c | 8.5 cd | 9.0 b |
| SuBL | P197L | 0.0 a | 0.0 a | 0.0 a | 9.0 c | 9.0 c | 9.0 c | 8.0 c | 9.0 b |
| SuRL | P197L | 0.0 a | 0.0 a | 8.6 b | 9.0 c | 9.0 c | 9.0 c | 8.5 cd | 9.0 b |
| Rhu426 | A205V | 6.5 b | 6.0 b | 9.0 b | 5.4 b | 2.0 b | 6.5 b | 7.0 b | 9.0 b |
| B770imi | A205V | 7.0 b | 6.0 b | 0.0 a | 5.0 b | 2.0 b | 6.0 b | n.d. | 9.0 b |
| RW-B | W574L | 0.0 a | 0.0 a | 0.0 a | 0.0 a | 0.0 a | 2.0 a | 0.0 a | 2.0 a |
| MS | | 108.6*** | 103.9*** | 135.21*** | 70.36*** | 103.4*** | 41.9*** | 58.4*** | 42.0*** |
| LSD | | 0.68 | 0.4558 | 0.4558 | 0.4558 | 0.001 | 0.68 | 0.72 | 0.54 |

FIG. 5

| Herbicide rate | F1 R S | F2 R S | Ratio tested | χ2 p-value | BC1F1 R S | Ratio tested | χ2 p-value |
|---|---|---|---|---|---|---|---|
| 80g a.i. ha-1 | 22 0 | 520 0 | - | - | 280 0 | - | - |
| 320g a.i. ha-1 | 18 0 | 381 127 | 3:1 | 0.837 | 151 146 | 1:1 | 0.77 |

FIG. 6

| F2 | Number of Plants | Haplotype segregation A/A | A/B | B/B |
|---|---|---|---|---|
| S | 30 | 0 | 0 | 30 |
| R | 81 | 26 | 55 | 0 |
| BC1F1 | | | | |
| S | 62 | 0 | 0 | 62 |
| R | 64 | 0 | 64 | 0 |

FIG. 7

ATGGCGGCTCCTCCCAACCCTTCCATCTCCTTCAAACCACCGTCACCCGCCGCCG
CACTGCCACCACGCTCCGCCTTCCTCCCCCGTTTCGCATTACCCATCACTTCCACT
ACCCAAAAACGACACCGTCTTCACATCTCCAATGTTCTCTCCGACTCCAAATCCA
CCACCACCACCACCACCACTCAACGACCGTTACCGGTGCAGCCTTTTGTCTC
CCGTTACGCGCCAGATCAACCGAGAAAGGCGCAGACGTGTTGGTGGAAGCTCT
AGAACGGGAAGGTGTCACCGACGTATTCGCCTACCCCGGCGGCGTCAATGGA
GATCCACCAAGCTCTCACGCGCTCAAACACTATCCGCAATGTCCTCCCCGTCAC
GAACAGGGCGGCGTGTTCGCCGCCGAAGGCTACGCACGCGCCTCCGGTCTTCCC
GGCGTGTGTATCGCCACTTCCGGTCCTGGAGCTACGAACCTAGTTAGTGGTCTTG
CTGACGCGCTGTTAGACAGTGTCCCCATGGTGGCAATCACCGGTCAAGTTCCCCG
GAGAATGATCGGAACCGATGCGTTTCAAGAAACCCCAATTGTTGAGGTAACACG
TTCGATTACTAAACATAATTATCTTGTGTTGGATGTTGAGGATATTCCCAGAATA
GTTCGTGAGGCTTTTTATCTTGCGAGCTCGGGTCGACCCGGCCCGGTTTTGATAG
ATGTACCGAAAGATATACAGCAACAGTTAGTGGTGCCGAAATGGGATGAACCGA
TGAGGTTACCGGGTTATTTGTCTAGAATGCCAAAGCCTCAATATGATGGGCATTT
GGAACAGATTGTTAGGTTGGTGGGGAAGCGAAGAGGCCGGTTTTGTATGTGGG
TGGTGGGTGTTTGAATTCGGATGATGAGTTGAGGCGGTTTGTGGAGCTTACGGGG
ATTCCGGTTGCGAGTACTTTGATGGGGCTCGGAGCGTACCCGGCTTCGAGTGATT
TGTCGCTTCATATGCTTGGGATGCATGGTACGGTTTATGCGAATTATGCGGTTGA
TAAGAGTGATTTGTTGCTTGCGTTTGGGGTGCGGTTTGATGACCGTGTGACGGGG
AAGCTTGAGGCGTTTGCTAGTAGGGCGAAGATTGTTCATATTGATATTGATCCGG
CTGAAATTGGGAAGAATAAACAGCCTCATGTGTCGATTTGTGGTGATATTAAGGT
CGCGTTACAGGGTTTGAACAAGATTTGGAGGAAAAGAATTCGGTGACTAATCTT
GATTTTCGAACTGGAGAAAGGAATTGGATGAACAAAAAGTGAAGTTCCCGTTG
AGCTTTAAAACGTTTGGCGAAGCGATTCCTCCACAGTATGCTATTCAAGTTCTTG
ATGAGTTAACGGGCGGGAATGCAATTATTAGCACCGGTGTCGGGCAACATCAGA
TGTGGGCTGCTCAGTTTTACAAATACAACAAACCTAGACAATGGCTGACGTCGGG
CGGGCTAGGGGCAATGGGTTTCGGCCTGCCCGCTGCTATCGGGGCGGCCGTTGCA
AGACCTGATGCGGTAGTAGTTGACATCGACGGTGACGGAAGCTTTATGATGAAT
GTTCAAGAGTTAGCCACAATCCGTGTTGAAAATCTGCCGGTTAAGATTTTATTAC
TTAACAATCAGCATTTGGGTATGGTGGTTCAGTTGGAGGATCGGTTTTACAAGGC
GAATCGGGCTCATACCTACTTAGGAAACCCGTCAAAAGAGTCGGAAATATTCCCT
AACATGGTGAAGTTTGCTGAAGCCTGTGATATCCCGGCTGCTCGAGTGACCCAAA
AGGCGGATCTACGAGCAGCTATTCAGAAGATGTTGGATACACCCGGGCCTTACTT
GTTGGATGTCATTGTGCCGCATCAAGAACACGTGTTGCCCATGATCCCGGCTGGC
GGAGGTTTCTCGGATGTGATCACCGAGGGTGATGGCAGAACGAAATATTGA

FIG. 8

MAAPPNPSISFKPPSPAAALPPRSAFLPRFALPITSTTQKRHRLHISNVLSDSKSTTTTTT
TTQRPLPVQPFVSRYAPDQPRKGADVLVEALEREGVTDVFAYPGGASMEIHQALTRS
NTIRNVLPRHEQGGVFAAEGYARASGLPGVCIATSGPGATNLVSGLADALLDSVPMV
AITGQVPRRMIGTDAFQETPIVEVTRSITKHNYLVLDVEDIPRIVREAFYLASSGRPGP
VLIDVPKDIQQQLVVPKWDEPMRLPGYLSRMPKPQYDGHLEQIVRLVGEAKRPVLY
VGGGCLNSDDELRRFVELTGIPVASTLMGLGAYPASSDLSLHMLGMHGTVYANYAV
DKSDLLLAFGVRFDDRVTGKLEAFASRAKIVHIDIDPAEIGKNKQPHVSICGDIKVAL
QGLNKILEEKNSVTNLDFSNWRKELDEQKVKFPLSFKTFGEAIPPQYAIQVLDELTGG
NAIISTGVGQHQMWAAQFYKYNKPRQWLTSGGLGAMGFGLPAAIGAAVARPDAVV
VDIDGDGSFMMNVQELATIRVENLPVKILLNNQHLGMVVQLEDRFYKANRAHTYL
GNPSKESEIFPNMVKFAEACDIPAARVTQKADLRAAIQKMLDTPGPYLLDVIVPHQE
HVLPMIPAGGGFSDVITEGDGRTKY

FIG. 9

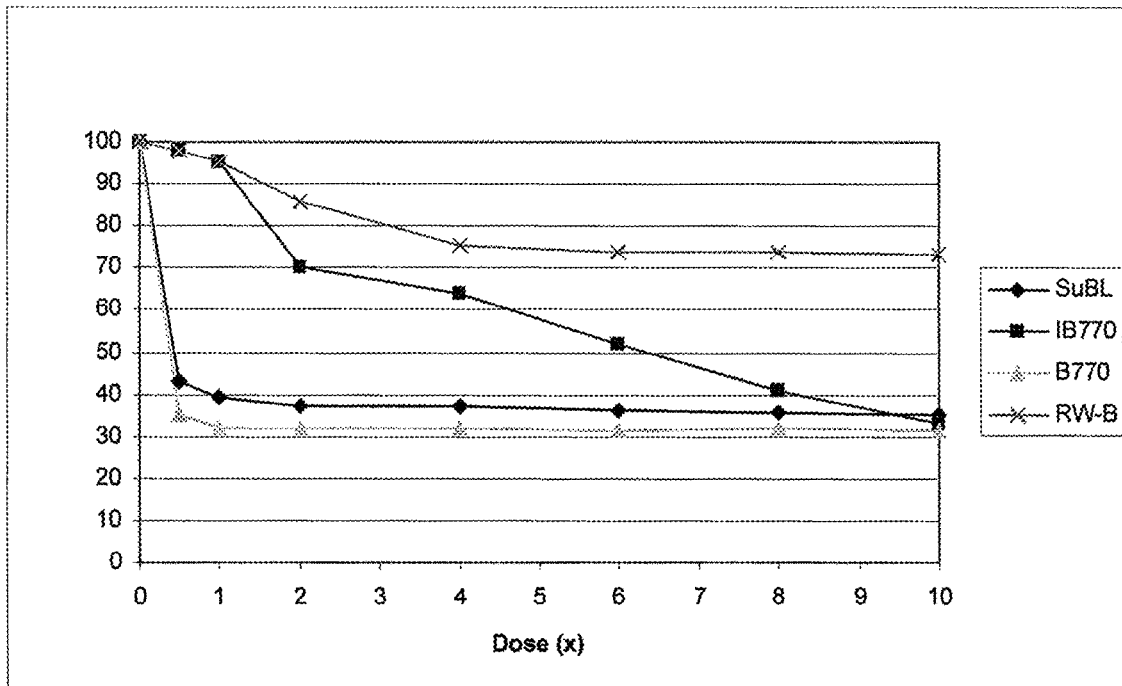

SEQUENCE LISTING

```
<160> NUMBER OF SEQ ID NOS: 18

<210> SEQ ID NO 1
<211> LENGTH: 1968
<212> TYPE: DNA
<213> ORGANISM: Helianthus annuus

<400> SEQUENCE: 1
atggcggctc tcccaaccc ttccatctcc ttcaaaccac cgtcaccgc cgccgcactg      60 ccaccacgct ccgccttcct ccccgtttc gcattaccca tcacttccac tacccaaaaa     120
cgacaccgtt tcacatctc caatgttctc tccgactcca aatccaccac caccaccacc    180
accaccactc aacgaccgtt accggtgcag cctttgtct cccgttacgc gccagatcaa     240
ccgagaaaag gcgcagacgt gttggtggaa gctctagaac gggaaggtgt caccgacgta    300
ttcgcctacc ccggcggcgc gtcaatggag atccaccaag ctctcacgcg ctcaaacact    360
atccgcaatg tcctccccg tcacgaacag ggcggcgtgt tcgccgccga aggctacgca    420
cgcgcctccg gtcttcccgg cgtgtgtatc gccacttccg gtcctggagc tacgaaccta    480
gttagtggtc ttgctgacgc gctgttagac agtgtcccca tggtggcaat caccggtcaa    540
gttccccgga gaatgatcgg aaccgatgcg tttcaagaaa ccccaattgt tgaggtaaca    600
cgttcgatta ctaaacataa ttatcttgtg ttggatgttg aggatattcc cagaatagtt    660
cgtgaggctt tttatcttgc gagctcgggt cgacccggcc cggttttgat agatgtaccg    720
aaagatatac agcaacagtt agtggtgccg aaatgggatg aaccgatgag gttaccgggt    780
```

-continued

```
tatttgtcta gaatgccaaa gcctcaatat gatgggcatt tggaacagat tgttaggttg      840 gtggggaag cgaagaggcc ggttttgtat gtgggtggtg ggtgtttgaa ttcggatgat       900
gagttgaggc ggtttgtgga gcttacgggg attccggttg cgagtacttt gatgggctc       960 ggagcgtacc cggcttcgag tgatttgtcg cttcatatgc ttgggatgca tggtacggtt     1020
tatgcgaatt atgcggttga taagagtgat ttgttgcttg cgtttggggt gcggtttgat     1080
gaccgtgtga cggggaagct tgaggcgttt gctagtaggg cgaagattgt tcatattgat     1140
attgatccgg ctgaaattgg gaagaataaa cagcctcatg tgtcgatttg tggtgatatt     1200
aaggtcgcgt tacagggttt gaacaagatt ttggaggaaa agaattcggt gactaatctt     1260 gattttcga actggagaaa ggaattggat gaacaaaaag tgaagttccc gttgagcttt      1320
aaaacgtttg gcgaagcgat tcctccacag tatgctattc aagttcttga tgagttaacg     1380
ggcgggaatg caattattag caccggtgtc gggcaacatc agatgtgggc tgctcagttt     1440
tacaaataca acaaacctag acaatggctg acgtcgggcg ggctagggc aatgggtttc      1500 ggcctgcccg ctgctatcgg ggcggccgtt gcaagacctg atgcgtagt agttgacatc      1560 gacggtgacg gaagctttat gatgaatgtt caagagttag ccacaatccg tgttgaaaat     1620
ctgccggtta agatttttatt acttaacaat cagcatttgg gtatggtggt tcagttggag    1680
gatcggtttt acaaggcgaa tcgggctcat acctacttag gaaacccgtc aaaagagtcg     1740
gaaatattcc ctaacatggt gaagtttgct gaagcctgtg atatcccggc tgctcgagtg     1800
acccaaaagg cggatctacg agcagctatt cagaagatgt tggatacacc cgggccttac     1860
ttgttggatg tcattgtgcc gcatcaagaa cacgtgttgc ccatgatccc ggctggcgga     1920
ggtttctcgg atgtgatcac cgagggtgat ggcagaacga aatattga                  1968
```

<210> SEQ ID NO 2
<211> LENGTH: 655
<212> TYPE: PRT
<213> ORGANISM: Helianthus annuus

<400> SEQUENCE: 2

```
Met Ala Ala Pro Pro Asn Pro Ser Ile Ser Phe Lys Pro Pro Ser Pro
1               5                   10                  15

Ala Ala Ala Leu Pro Pro Arg Ser Ala Phe Leu Pro Arg Phe Ala Leu
                20                  25                  30

Pro Ile Thr Ser Thr Thr Gln Lys Arg His Arg Leu His Ile Ser Asn
            35                  40                  45

Val Leu Ser Asp Ser Lys Ser Thr Thr Thr Thr Thr Thr Thr Thr Gln
        50                  55                  60

Arg Pro Leu Pro Val Gln Pro Phe Val Ser Arg Tyr Ala Pro Asp Gln
65                  70                  75                  80

Pro Arg Lys Gly Ala Asp Val Leu Val Glu Ala Leu Glu Arg Glu Gly
                85                  90                  95

Val Thr Asp Val Phe Ala Tyr Pro Gly Gly Ala Ser Met Glu Ile His
            100                 105                 110

Gln Ala Leu Thr Arg Ser Asn Thr Ile Arg Asn Val Leu Pro Arg His
        115                 120                 125

Glu Gln Gly Gly Val Phe Ala Ala Glu Gly Tyr Ala Arg Ala Ser Gly
    130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
```

```
                    165                 170                 175
Ile Thr Gly Gln Val Pro Arg Arg Met Ile Gly Thr Asp Ala Phe Gln
                180                 185                 190
Glu Thr Pro Ile Val Glu Val Thr Arg Ser Ile Thr Lys His Asn Tyr
            195                 200                 205
Leu Val Leu Asp Val Glu Asp Ile Pro Arg Ile Val Arg Glu Ala Phe
        210                 215                 220
Tyr Leu Ala Ser Ser Gly Arg Pro Gly Pro Val Leu Ile Asp Val Pro
225                 230                 235                 240
Lys Asp Ile Gln Gln Gln Leu Val Val Pro Lys Trp Asp Glu Pro Met
                245                 250                 255
Arg Leu Pro Gly Tyr Leu Ser Arg Met Pro Lys Pro Gln Tyr Asp Gly
                260                 265                 270
His Leu Glu Gln Ile Val Arg Leu Val Gly Glu Ala Lys Arg Pro Val
            275                 280                 285
Leu Tyr Val Gly Gly Gly Cys Leu Asn Ser Asp Asp Glu Leu Arg Arg
        290                 295                 300
Phe Val Glu Leu Thr Gly Ile Pro Val Ala Ser Thr Leu Met Gly Leu
305                 310                 315                 320
Gly Ala Tyr Pro Ala Ser Ser Asp Leu Ser Leu His Met Leu Gly Met
                325                 330                 335
His Gly Thr Val Tyr Ala Asn Tyr Ala Val Asp Lys Ser Asp Leu Leu
            340                 345                 350
Leu Ala Phe Gly Val Arg Phe Asp Asp Arg Val Thr Gly Lys Leu Glu
        355                 360                 365
Ala Phe Ala Ser Arg Ala Lys Ile Val His Ile Asp Ile Asp Pro Ala
370                 375                 380
Glu Ile Gly Lys Asn Lys Gln Pro His Val Ser Ile Cys Gly Asp Ile
385                 390                 395                 400
Lys Val Ala Leu Gln Gly Leu Asn Lys Ile Leu Glu Glu Lys Asn Ser
                405                 410                 415
Val Thr Asn Leu Asp Phe Ser Asn Trp Arg Lys Glu Leu Asp Glu Gln
            420                 425                 430
Lys Val Lys Phe Pro Leu Ser Phe Lys Thr Phe Gly Glu Ala Ile Pro
        435                 440                 445
Pro Gln Tyr Ala Ile Gln Val Leu Asp Glu Leu Thr Gly Gly Asn Ala
        450                 455                 460
Ile Ile Ser Thr Gly Val Gly Gln His Gln Met Trp Ala Ala Gln Phe
465                 470                 475                 480
Tyr Lys Tyr Asn Lys Pro Arg Gln Trp Leu Thr Ser Gly Gly Leu Gly
                485                 490                 495
Ala Met Gly Phe Gly Leu Pro Ala Ala Ile Gly Ala Ala Val Ala Arg
                500                 505                 510
Pro Asp Ala Val Val Val Asp Ile Asp Gly Asp Gly Ser Phe Met Met
            515                 520                 525
Asn Val Gln Glu Leu Ala Thr Ile Arg Val Glu Asn Leu Pro Val Lys
        530                 535                 540
Ile Leu Leu Leu Asn Asn Gln His Leu Gly Met Val Val Gln Leu Glu
545                 550                 555                 560
Asp Arg Phe Tyr Lys Ala Asn Arg Ala His Thr Tyr Leu Gly Asn Pro
                565                 570                 575
Ser Lys Glu Ser Glu Ile Phe Pro Asn Met Val Lys Phe Ala Glu Ala
            580                 585                 590
```

```
Cys Asp Ile Pro Ala Ala Arg Val Thr Gln Lys Ala Asp Leu Arg Ala
        595                 600                 605

Ala Ile Gln Lys Met Leu Asp Thr Pro Gly Pro Tyr Leu Leu Asp Val
    610                 615                 620

Ile Val Pro His Gln Glu His Val Leu Pro Met Ile Pro Ala Gly Gly
625                 630                 635                 640

Gly Phe Ser Asp Val Ile Thr Glu Gly Asp Gly Arg Thr Lys Tyr
                645                 650                 655

<210> SEQ ID NO 3
<211> LENGTH: 123
<212> TYPE: DNA
<213> ORGANISM: Helianthus annuus

<400> SEQUENCE: 3
gaaaatctgc cggttaagat tttattactt aacaaccagc atttgggtat ggtggttcag      60
tgggaggatc ggttttacaa ggcgaatcgg gctcatacct acttaggaaa cccgtcaaaa     120
gag                                                                   123

<210> SEQ ID NO 4
<211> LENGTH: 123
<212> TYPE: DNA
<213> ORGANISM: Helianthus annuus

<400> SEQUENCE: 4
gaaaatctgc cggttaagat tttattactt aacaaccagc atttgggtat ggtggttcag      60
tgggaggatc ggttttacaa ggcgaatcgg gctcatacct acttaggaaa cccgtcaaaa     120
gag                                                                   123

<210> SEQ ID NO 5
<211> LENGTH: 123
<212> TYPE: DNA
<213> ORGANISM: Helianthus annuus

<400> SEQUENCE: 5
gaaaatctgc cggttaagat tttattactt aacaatcagc atttgggtat ggtggttcag      60
ttggaggatc ggttttacaa ggcgaatcgg gctcatacct acttaggaaa cccgtcaaaa     120
gag                                                                   123

<210> SEQ ID NO 6
<211> LENGTH: 123
<212> TYPE: DNA
<213> ORGANISM: Xanthium spp

<400> SEQUENCE: 6
gaaaatcttc ctgttaagat tttgttactt aacaatcagc atttgggtat ggtggttcag      60
tgggaggatc ggttttacaa ggcgaatcgg gctcatacct acttaggaaa tccgtcaaaa     120
gag                                                                   123

<210> SEQ ID NO 7
<211> LENGTH: 123
<212> TYPE: DNA
<213> ORGANISM: Arabidopsis thaliana

<400> SEQUENCE: 7
gagcaacttc cagtgaagat actcttatta acaaccagc atcttggcat ggttatgcaa       60
```

```
tgggaagatc ggttttacaa ggctaaccga gctcacacat ttctcgggga tccggctcag    120
gag                                                                  123
```

<210> SEQ ID NO 8
<211> LENGTH: 41
<212> TYPE: PRT
<213> ORGANISM: Helianthus annuus

<400> SEQUENCE: 8

```
Glu Asn Leu Pro Val Lys Ile Leu Leu Asn Asn Gln His Leu Gly
1               5                   10                  15

Met Val Val Gln Trp Glu Asp Arg Phe Tyr Lys Ala Asn Arg Ala His
        20                  25                  30

Thr Tyr Leu Gly Asn Pro Ser Lys Glu
        35                  40
```

<210> SEQ ID NO 9
<211> LENGTH: 41
<212> TYPE: PRT
<213> ORGANISM: Helianthus annuus

<400> SEQUENCE: 9

```
Glu Asn Leu Pro Val Lys Ile Leu Leu Asn Asn Gln His Leu Gly
1               5                   10                  15

Met Val Val Gln Trp Glu Asp Arg Phe Tyr Lys Ala Asn Arg Ala His
        20                  25                  30

Thr Tyr Leu Gly Asn Pro Ser Lys Glu
        35                  40
```

<210> SEQ ID NO 10
<211> LENGTH: 41
<212> TYPE: PRT
<213> ORGANISM: Helianthus annuus

<400> SEQUENCE: 10

```
Glu Asn Leu Pro Val Lys Ile Leu Leu Asn Asn Gln His Leu Gly
1               5                   10                  15

Met Val Val Gln Leu Glu Asp Arg Phe Tyr Lys Ala Asn Arg Ala His
        20                  25                  30

Thr Tyr Leu Gly Asn Pro Ser Lys Glu
        35                  40
```

<210> SEQ ID NO 11
<211> LENGTH: 41
<212> TYPE: PRT
<213> ORGANISM: Xanthium spp

<400> SEQUENCE: 11

```
Glu Asn Leu Pro Val Lys Ile Leu Leu Asn Asn Gln His Leu Gly
1               5                   10                  15

Met Val Val Gln Trp Glu Asp Arg Phe Tyr Lys Ala Asn Arg Ala His
        20                  25                  30

Thr Tyr Leu Gly Asn Pro Ser Lys Glu
        35                  40
```

<210> SEQ ID NO 12
<211> LENGTH: 41
<212> TYPE: PRT
<213> ORGANISM: Arabidopsis thaliana

<400> SEQUENCE: 12

```
Glu Gln Leu Pro Val Lys Ile Leu Leu Asn Asn Gln His Leu Gly
1               5                   10                  15

Met Val Met Gln Trp Glu Asp Arg Phe Tyr Lys Ala Asn Arg Ala His
            20                  25                  30

Thr Phe Leu Gly Asp Pro Ala Gln Glu
        35                  40

<210> SEQ ID NO 13
<211> LENGTH: 19
<212> TYPE: DNA
<213> ORGANISM: Helianthus annuus

<400> SEQUENCE: 13
atggcggctc ctcccaacc                                            19

<210> SEQ ID NO 14
<211> LENGTH: 21
<212> TYPE: DNA
<213> ORGANISM: Helianthus annuus

<400> SEQUENCE: 14
cggtaacctc atcggttcat c                                         21

<210> SEQ ID NO 15
<211> LENGTH: 21
<212> TYPE: DNA
<213> ORGANISM: Helianthus annuus

<400> SEQUENCE: 15
gatgaaccga tgaggttacc g                                         21

<210> SEQ ID NO 16
<211> LENGTH: 21
<212> TYPE: DNA
<213> ORGANISM: Helianthus annuus

<400> SEQUENCE: 16
tccgcctttt gggtcactcg a                                         21

<210> SEQ ID NO 17
<211> LENGTH: 22
<212> TYPE: DNA
<213> ORGANISM: Helianthus annuus

<400> SEQUENCE: 17
ggtgactaat cttgattttt cg                                        22

<210> SEQ ID NO 18
<211> LENGTH: 20
<212> TYPE: DNA
<213> ORGANISM: Hellianthus annuus

<400> SEQUENCE: 18
tcaatatttc gttctgccat                                           20
```

US 8,952,222 B2

HERBICIDE RESISTANT SUNFLOWER PLANTS DERIVED FROM RW-B CULTIVAR

CROSS-REFERENCE TO RELATED APPLICATIONS

This application is a U.S. National Stage entry of International Application No. PCT/NL2009/050468, filed on Jul. 30, 2009, and claims benefit of U.S. Ser. No. 61/085,224, filed on Jul. 31, 2008. The disclosures of the above-identified applications are incorporated herein by reference in their entirety.

FIELD OF THE INVENTION

This present invention relates to the field of agricultural biotechnology, particularly to herbicide-resistant sunflower plants containing novel polynucleotide sequences that encode herbicide-resistant sunflower acetohydroxyacid synthase large subunit proteins.

BACKGROUND

Acetolactate synthase (ALS) or acetohydroxyacid synthase (AHAS) is the first enzyme in the biosynthetic pathway of the branched chain amino acids valine, leucine and isoleucine in plants and microorganisms. Five distinct families of compounds inhibit the AHAS enzyme and are used as nonselective, broad-spectrum herbicides: sulfonylureas (SUs), imidazolinones (IMIs), triazolopyrimidines (TPs), sulfonylaminocarbonyltriazolinones (SCTs) and pyrimidinyloxybenzoates (POBs).

Given their high effectiveness and low-toxicity, certain herbicides are favored for agricultural use. However, the ability to use some of these herbicides in a particular crop production system depends upon the availability of resistant varieties of the crop plant of interest. To produce such resistant varieties, plant breeders need to develop breeding lines with the resistance traits. Accordingly, herbicide resistant breeding lines and varieties of crop plants, as well as methods and compositions for the production and use of resistant breeding lines and varieties, are needed.

SUMMARY

Sunflower plants having multiple herbicide resistance are provided. The plants are resistant to at least an imidazolinone herbicide, a sulfonylurea herbicide, a triazolopyrimidine herbicide, and a pyrimidinyloxybenzoate herbicide and mixtures of these herbicides. Advantageously, the seeds of the plant have an oil content that is greater than 40%, a seed yield that is more than one tonne per hectare, and/or a sunflower plant having a single head. In other embodiments, the plants have combinations of these characteristics. In some embodiments, the resistant plants have an AHAS gene that encodes a mutation at amino acid 574 or its equivalent, that apparently confers the resistant trait, where the mutation may be the replacement of a tryptophan at that position with another amino acid, for example leucine. Specific embodiments include plants containing an AHASL1 gene having the nucleotide sequence set forth in SEQ ID NO: 1, or an AHASL1 protein having the amino acid sequence set forth in SEQ ID NO: 2.

Isolated nucleic acid molecules encoding mutant AHASL1 genes also are provided, for example an isolated nucleic acid containing a sequence SEQ ID NO: 1. Also provided are plant cells stably transformed with a nucleic acid having the sequence of SEQ ID NO: 1, and transgenic sunflower plant containing a transgene containing SEQ ID NO: 1. In other embodiments, the plants contain an expression cassette having a promoter active in sunflower plants that is operably linked to an isolated nucleic acid encoding a protein having the sequence encoded by SEQ ID NO: 1.

Also provided are methods for controlling weeds within the vicinity of a resistant sunflower plant of the type described above, by applying a herbicide to the weeds and the sunflower plant, where the herbicide is an imidazolinone herbicide, a sulfonylurea herbicide, a triazolopyrimidine herbicide, or a pyrimidinyloxybenzoate herbicide, or mixtures of these herbicides.

Also provided are sunflower seeds and the plant grown from those seeds. The plants have herbicide resistance to an imidazolinone herbicide, a sulfonylurea herbicide, a triazolopyrimidine herbicide, a pyrimidinyloxybenzoate herbicide and mixtures thereof. In specific embodiments, the plants grown from the seed have a seed oil content that is greater than 40%, a seed yield that is more than one tonne per hectare, and/or a sunflower plant having a single head. Further embodiments include combinations of the aforementioned features. These plants may contain a mutant AHASL1 as described above.

Also provided herein are methods for improving herbicide tolerance in a sunflower plant. Preferred embodiments include regenerating a sunflower cell into a sunflower plant where the sunflower cell is transformed with a construct having a nucleic acid sequence encoding the protein encoded by SEQ ID NO: 1, regenerating the sunflower cell into a sunflower plant and selecting fertile flower plants that are vegetative and reproductive resistant to an effective dose of herbicide. The herbicide is selected from the group consisting of a sulfonylurea, an imidazolinone, a pyrimidinyloxybenzoates, a triazolopyrimidine, and mixtures thereof.

Also provided herein are methods for producing a herbicide resistant sunflower plant by back crossing. Preferred embodiments include crossing a first sunflower plant having herbicide resistant AHAS activity to a second sunflower plant not having herbicide resistant AHAS activity where the first sunflower plant has a nucleic acid encoding the protein encoded by SEQ ID NO: 1. Advantageously, progeny plants having herbicide resistant AHAS activity are selected. Further preferred embodiments include a seed having the herbicide resistant characteristics of the first sunflower plant.

In a specific embodiment, a seed of sunflower cultivar designated RW-B is provided. This seed and corresponding plant have all the physiological, herbicide-resistant, and morphological characteristics described above, more particularly, the regenerated plant from cultivar RW-B is homozygous for the genotypic characteristics of (i) a mutant AHAS gene wherein said mutant gene encodes a AHAS protein with a mutation at amino acid 574 or its equivalent, wherein amino acid 574 or its equivalent is an amino acid other than tryptophan and (ii) a mutant AHAS gene which encodes an AHAS protein which has the amino acid sequence of SEQ ID NO: 2; the morphological characteristics of a single head; and the physiological characteristics of (i) combined resistance to an imidazolinone herbicide, a sulfonylurea herbicide, a sulfonylurea herbicide, a triazolopyrimidine herbicide, a pyrimidinyloxybenzoate herbicide and mixtures thereof, (ii) resistance to cloransulam-methyl present in a concentration of at least 67 grams of active ingredient per hectare, (iii) resistance to the mixture of imzapyr present in a concentration of at least 160 grams per hectare and metsulfuron present in a concentration of at least 10 grams per hectare, (iv) produces a seed having an oil content of greater than 40% and (v) the yield from said sunflower plant is greater than one tonne per hectare. A representative seed of this sunflower cultivar has been deposited at the American Type Culture Collection (ATCC) under Accession No: PTA-9176. The deposit will be maintained under the terms of the Budapest Treaty on the International Recognition for the Purposes of Patent Procedure. The deposit of the seed of the RW-B cultivar was made for a term of at least 30 years and at least 5 years after the most recent request for the furnishing of a sample of the deposit is received by the ATCC. Additionally, Applicants have satisfied all the requirements of 37 C.F.R. §§1.801-1.809, including providing an indication of the viability of the sample.

Also provided is a tissue culture of regenerable cells of the aforementioned resistant sunflower plants. Preferred embodiments include tissue cultures where the cells of the tissue culture comprise a leaf, pollen, an embryo, a cotyledon, a hypocotyl, meristematic cells, a root, a root tip, an anther, a flower, a seed, a stem, ovules, shoots, stems, stalks, pith capsules or a pod. Resistant sunflower plants may be grown from the aforementioned tissue culture and express all of the morphological and physiological characteristics of sunflower cultivar RW-B.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION THE DRAWINGS

FIG. 1 shows the partial DNA sequence alignment of the coding region of the AHASL1 gene from HA89 (GenBank acc. no. AY541451) (SEQ ID NO: 3), B770 line (SEQ ID NO: 4), resistant line RW-B (SEQ ID NO: 5), *Xanthium* sp. ALS gene (GenBank acc. no. U16280) (SEQ ID NO: 6) and *Arabidopsis thaliana* AHAS gene (GenBank acc. no. AY124092) (SEQ ID NO: 7).

FIG. 2 shows the partial amino acid sequence alignment of the AHASL1 protein from HA89 (GenBank acc. no. AY541451) (SEQ ID NO: 8), B770 line (SEQ ID NO: 9), resistant line RW-B (SEQ ID NO: 10), *Xanthium* sp. ALS gene (GenBank acc. no. U16280) (SEQ ID NO: 11) and *Arabidopsis thaliana* AHAS gene (GenBank acc. no. AY124092) (SEQ ID NO: 12).

FIG. 3 shows the inheritance of IMI resistance in RW-B.

FIG. 4 shows the phytotoxicity index of seven sunflower lines sprayed with different AHAS-inhibiting herbicides in table form.

FIG. 5 shows the response of sunflower plants, Resistant (R) and Susceptible (S), to imazapyr in an allelism test in $F_1$, $F_2$ and $BC_1F_1$ generations FIG. 6 shows AHASI haplotype segregation and the reaction of sunflower plants, Resistant (R) and Susceptible (S), to imazapyr applied at a rate of 320 g a.i. $ha^{-1}$ FIG. 7 shows the complete nucleotide sequence of the AHASL1 gene of the line RW-B (SEQ ID NO: 1).

FIG. 8 shows the complete amino acid sequence of the AHASL1 gene of the line RW-B (SEQ ID NO: 2).

FIG. 9 shows height reduction (as percentage of the untreated control plants) for 4 lines carrying different mutant alleles at the AHASL1 locus of sunflower 14 days after application of increased rates of imazapyr.

Figure 10:
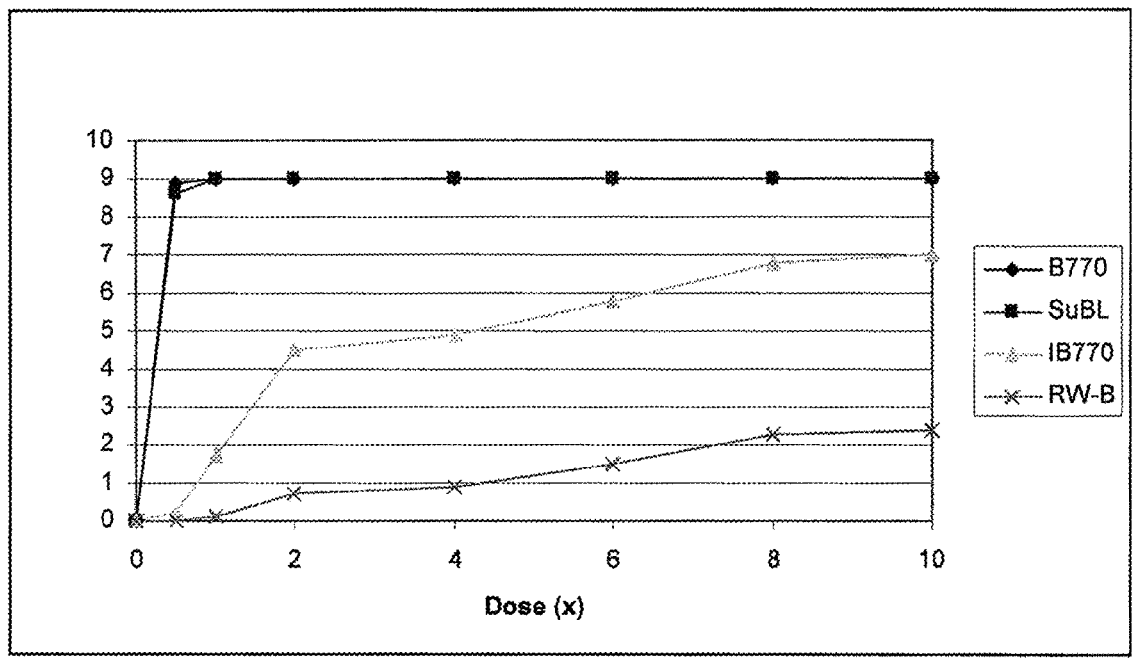

FIG. 10 shows the phytotoxicity Index for 4 sunflower lines carrying different mutant alleles at the AHASL1 locus of sunflower when challenged with increased rates of imazapyr.

Figure 11:
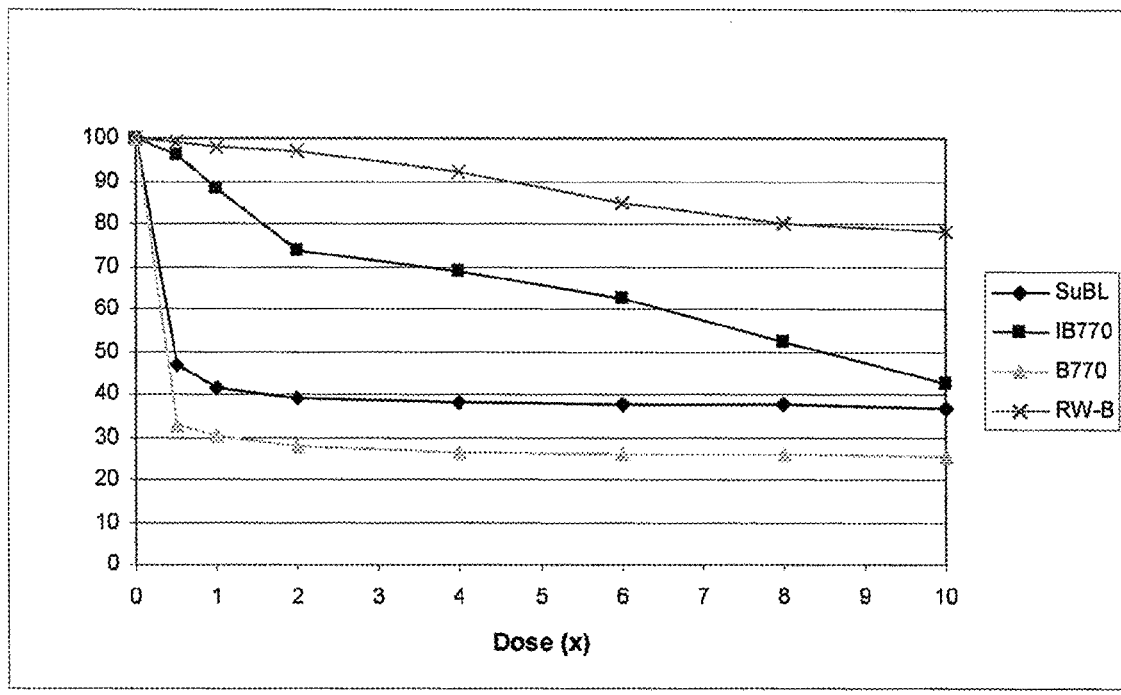

FIG. 11 show dose response curves for above ground dry weight biomass (as percentage of the untreated control plants) for 4 sunflower lines carrying different mutant alleles at the AHASL1 locus when challenged with increased rates of imazapyr.

Figure 12:
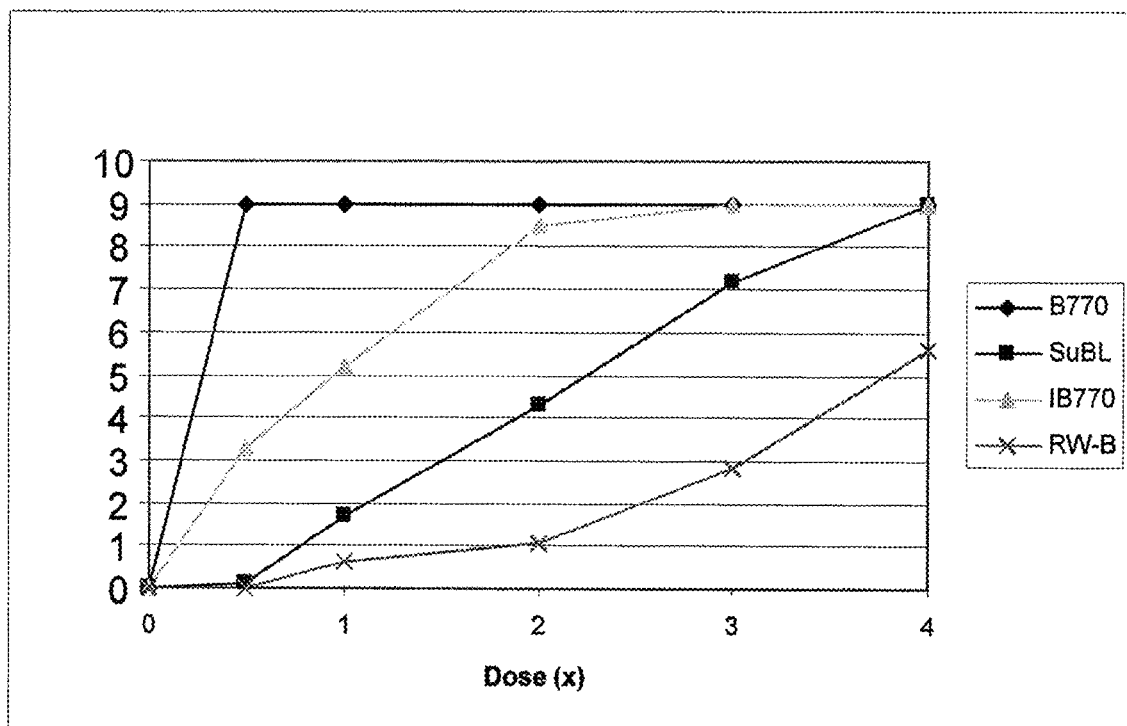

FIG. 12 shows the phytotoxicity Index for 4 sunflower lines carrying different mutant alleles at the AHASL1 locus of sunflower when challenged with increased rates metsulfuron.

Figure 13:
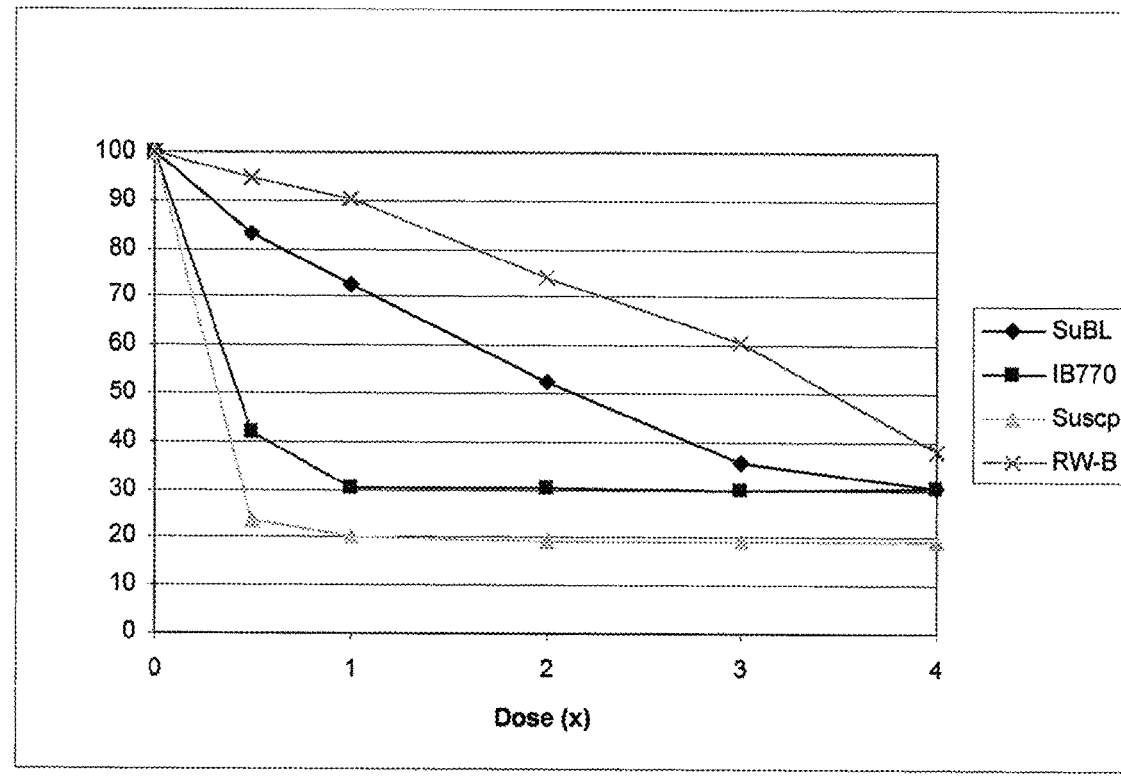

FIG. 13 shows dose response curves for above ground dry weight biomass (as percentage of the untreated control plants) for 4 sunflower lines carrying different mutant alleles at the AHASL1 locus when challenged with increased rates of metsulfuron.

DETAILED DESCRIPTION

Sunflower plants having increased resistance to herbicides relative to wild-type sunflower plants are provided. These plants contain a new genetic mutation in the AHAS gene which confers broad-spectrum resistance to AHAS-inhibiting herbicides, and this mutation has been identified and characterized. The availability of this new mutation, coupled with the use of available AHAS-inhibiting herbicides, provides a herbicide-tolerant sunflower crop production system and represents a new and powerful weed control option for sunflower growers.

The present inventors surprisingly have found that a new mutation at codon 574 (*Arabidopsis thaliana* nomenclature) of the sunflower AHASL1 gene confers high levels, and broad spectrum resistance to at least four out of the five families of AHAS-inhibitor herbicides. See Sala, C. A., Bulos, M, Echarte, A. M., Whitt. S. & Ascenzi, R. 2008, Molecular and biochemical characterization of an induced mutation conferring imidazolinone resistance in sunflower, *Theor. Appl. Genet.*, 118:105-112. This single mutation, which changes a tryptophan to a leucine in the AHAS protein, is responsible for this remarkable breadth of herbicide resistance where the sunflowers of the invention unexpectedly have resistance to all of the herbicides IMI, SU, TP and POB. Accordingly, this new mutation provides a number of technological advantages over all the resistant mutations presently known in sunflower. These advantages include, but are not limited to the ability to: apply new types of herbicides to sunflower crops that ordinarily could not be applied without adversely affecting the sunflower itself; apply a mixture of two or more herbicides concurrently to sunflower crops that otherwise would not be combinable; vary the time and type of herbicide application to sunflower; and apply more than one herbicide post emergence due to carry-over resistance.

Methods are provided for combating undesired vegetation or controlling weeds by treating the sunflower seeds of the resistant plants with an AHAS-inhibiting herbicide or a mixture of herbicides before sowing and/or after pre-germination. The treated seeds are then sown, for example, in soil in a field or in a potting medium in greenhouse. The resulting plants also can be treated with an AHAS-inhibiting herbicide or a mixture of herbicides to combat undesired vegetation and/or to control weeds in the immediate vicinity of the sunflower plants.

Marker-assisted backcrossing experiments allowed for the development of commercially useful multiple herbicide resistant sunflower plants described herein. In backcrossing, direct selection may be applied where a genetic locus acts as a partially dominant trait such as with the herbicide resistance trait. To select for the sunflower plants of the inventions, the progeny of the initial cross were sprayed with the herbicide prior to the backcrossing. The spraying eliminated plants that did not have the desired herbicide resistance characteristic, and the plants having the herbicide resistance gene were used in subsequent backcrosses. This process was repeated for all additional backcross generations, until plants that bred true for multiple herbicide resistance were obtained.

In addition to herbicide resistance, the sunflower plants also have a number of other advantageous characteristics. Thus, the sunflower seeds have one or more of the following characteristics, an oil content greater than 40%, a seed yield more than one tonne per hectare, and a sunflower plant having a single head. Surprisingly, these characteristics are found in combinations with each other and with the broad spectrum herbicide resistance conferred by the mutation at codon 574.

Because the sunflower plants described herein are, remarkably, resistant to four or more families of herbicides, farmers can treat the crops with a wider range of herbicides than were previously available for use with sunflowers. Controlling weeds in sunflower crops is required to avoid poor growth and yield loss and the ability to use more than one herbicide at the same or at different times during the growing season provides significant weed control advantages over conventional sunflower varieties. For example, because sunflowers grown from seeds can take up to two weeks to appear, weeds can very easily establish themselves and then shade the sunflower seedlings, which will stunt the sunflowers' growth. Without control, weed competition in sunflower crops leads to major economic losses to growers because of a yield reductions reaching as high as 50%. The plants of the present invention avoid these concerns because their resistance to more than one existing herbicide family allows for enhanced herbicide application protocols.

A further advantage of herbicide resistance to multiple families of herbicides is that farmers can commercially exploit of sunflower crops without the added expense of developing new herbicides. New sunflower crop herbicides are unlikely to be developed due to the high cost of herbicide registration. Multiple resistances to known herbicides is also advantageous for sunflower crops susceptible to injury from carryover. Carryover occurs when the herbicides from the previous crop impairs the growth of the current crop. Having resistance to multiple herbicides reduces the damage done to sunflower crops from carryover. Further, the increased ability to control weeds in the sunflower plants of the invention means that future weed problems in the crops grown after the sunflowers also are limited.

In the context of the present invention, the terms "herbicide-tolerant" and "herbicide-resistant" are used interchangeably and have an equivalent meaning and an equivalent scope. Similarly, the terms "herbicide-tolerance" and "herbicide-resistance" are used interchangeably and have an equivalent meaning and an equivalent scope. Likewise, the terms for the families of herbicides, for example "imidazolinone-resistant" and "imidazolinone-resistance," are used interchangeably and have equivalent meanings and scopes as the terms "imidazolinone-tolerant" and "imidazolinone-tolerance," respectively.

Herbicide-resistant AHASL polynucleotides and herbicide-resistant AHASL proteins are provided. The term "herbicide-resistant AHASL polynucleotide" means, for purposes of this invention, a polynucleotide that encodes a protein comprising herbicide-resistant AHAS activity. A "herbicide-tolerant AHASL protein" or "herbicide-resistant AHASL protein," is an AHASL protein that displays measurably higher AHAS activity, relative to the AHAS activity of a wild-type AHASL protein, when in the presence of at least one herbicide that is known to interfere with AHAS activity and at a concentration or level of the herbicide that is to known to inhibit the AHAS activity of the wild-type AHASL protein. A "herbicide-tolerant" or "herbicide-resistant" plant is a plant that is tolerant or resistant to at least one herbicide, applied at a specific amount, that would normally kill or inhibit the growth of a normal or wild-type plant. In one embodiment, the herbicide-tolerant plants of the present invention comprise a herbicide-tolerant or herbicide-resistant AHASL protein. Although recent publications suggest different nomenclature designations, here and throughout, the term AHASL will be used to represent the catalytic or large (L) subunit of the AHAS enzyme. See e.g., Duggleby et al., 2008 *Plant Physiol. Biochem.* 46: 309-324.

Further, a herbicide-tolerant or herbicide-resistant AHASL protein can be introduced into a sunflower plant by transforming a plant or ancestor thereof with a nucleotide sequence encoding a herbicide-tolerant or herbicide-resistant AHASL protein. Such herbicide-tolerant or herbicide-resistant AHASL proteins are encoded by the herbicide-tolerant or herbicide-resistant AHASL polynucleotides. Alternatively, a herbicide-tolerant or herbicide-resistant AHASL protein may occur in a sunflower plant as a result of a naturally occurring or induced mutation in an endogenous AHASL gene in the genome of a plant or progenitor thereof. The present invention provides sunflower plants, plant tissues, plant cells, and host cells with increased resistance or tolerance to one or more herbicide, including but not limited to an IMI herbicide, a SU herbicide, a TP herbicide, a POB herbicide. Advantageously, the plants have increased resistance or tolerance to two or more of the above herbicides and, more advantageously, increased resistance or tolerance to three or more of the above herbicides. Most advantageously, the plants have increased resistance or tolerance to four or more of the above herbicides.

The preferred amount or concentration of the herbicide that is applied to the plants or the seeds as described herein is an "effective amount" or "effective concentration." The terms "effective amount" and "effective concentration" mean, for purposes of this invention, an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, an effective amount of an herbicide is an amount that is routinely used in agricultural production systems to kill weeds of interest. Such an amount is known to those of ordinary skill in the art. A wild-type, plant, plant tissue, plant cell or host cell" is a plant, plant tissue, plant cell, or host cell, respectively, that lacks the herbicide-resistance characteristics and/or particular polynucleotide of the invention. The term "wild-type" does not imply that a plant, plant tissue, plant cell, or other host cell lacks recombinant DNA in its genome, and/or does not possess herbicide-resistant characteristics that are different from those described herein. The term "plant" is intended to mean a plant at any developmental stage, as well as any part or parts of a plant that may be attached to or separate from a whole intact plant. Such parts of a plant include, but are not limited to, organs, tissues, and cells of a plant. Examples of particular plant parts include a stem, a leaf, a root, an inflorescence, a flower, a floret, a fruit, a pedicle, a peduncle, a stamen, an anther, a stigma, a style, an ovary, a petal, a sepal, a carpel, a root tip, a root cap, a root hair, a leaf hair, a seed hair, a pollen grain, a microspore, a cotyledon, a hypocotyl, an epicotyl, xylem, phloem, parenchyma, endosperm, a companion cell, a guard cell, and any other known organs, tissues, and cells of a plant. Furthermore, it is recognized that a seed is a plant.

The present invention describes a sunflower plant having increased resistance to an IMI herbicide, a SU herbicide, a TP herbicide, a POB herbicide, and/or mixtures thereof as compared to a wild type variety of the plant. Provided herein is a detailed description of the breeding and selection of sunflower plants having such increased resistance to an IMI herbicide, a SU herbicide, a TP herbicide, a POB herbicide, and/or mixtures thereof. One plant derived from these procedures is deposited with the ATCC (Patent Deposit Designation Number PTA-9176) and designated herein as the RW-B sunflower variety. A deposit of 2500 seeds of the RW-B sunflower variety was made with the American Type Culture Collection on Apr. 25, 2008. This deposit was made in accordance with the terms and provisions of the Budapest Treaty relating to the deposit of microorganisms. The deposit was made for a term of at least thirty years and at least five years after the most recent request for the furnishing of a sample of the deposit is received by the ATCC.

The sunflower plants of the present invention include both non-transgenic plants and transgenic plants. A "non-transgenic plant" is a plant lacking recombinant DNA in its genome. A "transgenic plant" is a plant comprising recombinant DNA in its genome and can be produced by introducing recombinant DNA into the genome of the plant. When such recombinant DNA is incorporated into the genome of the transgenic plant, progeny of the plant can also comprise the recombinant DNA. A progeny plant that comprises at least a portion of the recombinant DNA of at least one progenitor transgenic plant is also a transgenic plant. An example of a non-transgenic sunflower plant having increased resistance to an IMI herbicide, a SU herbicide, a TP herbicide, a POB herbicide, and/or mixtures thereof is the sunflower plant sunflower plant RW-B or a genetically engineered derivative of the sunflower plant RW-B, or of any progeny of the sunflower plant RW-B, or a plant that comprises the herbicide tolerance characteristics of the sunflower plant RW-B.

Sunflower plants can be propagated through tissue and cell culture techniques. Essentially any plant tissue with cells capable of cell division can be used for plant propagation through tissue and cell culture techniques. Cultures can be started from a leaf, pollen, an embryo, a cotyledon, a hypocotyl, meristematic cells, a root, a root tip, an anther, a flower, a seed, a stem, ovules, shoots, stems, stalks, pith capsules or a pod. Tissues taken from the vascular area of stems and roots are particularly suitable. U.S. Pat. Nos. 4,670,391, 4,670,392, 4,673,648, 4,681,849, 4,687,743 and 5,030,572 describe methods for regenerating sunflower plants from cell cultures derived from sunflower tissues. The state of the art is such that exemplary methods of obtaining sunflower plants from cell cultures and tissue cultures are now well known to one of ordinary skill in the art. A variety of plant culture techniques may be used to regenerate whole plants, such as are described in Gamborg and Phillips, "Plant Cell, Tissue and Organ Culture, Fundamental Methods", Springer Berlin, 1995); Evans et al. "Protoplasts Isolation and Culture", Handbook of Plant Cell Culture, Macmillian Publishing Company, New York, 1983; or Binding, "Regeneration of Plants, Plant Protoplasts", CRC Press, Boca Raton, 1985; or in Klee et al., Ann. Rev. of Plant Phys. 38:467 (1987). Detailed descriptions of culture systems for *Helianthus annuus* can be found in Chapter 11, *Sunflower* Biotechnology, Bidney, D. L. and Scelonge, C. J., pp. 559-593 and references cited therein, Sunflower Technology and Production, edited by A. A. Schneiter, Agronomy 35, publishers, American Society of Agronomy Inc. 1997, Transformation of Sunflower, all of which are herein incorporated by reference.

Herbicide-resistant sunflower plants can be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company, the disclosure of which is incorporated herein by reference.

A Mutant Gene and its Encoded Protein Confer Broad Herbicide Resistance on Sunflower Plants The present inventors have found that substituting for the tryptophan at amino acid position 574, or equivalent position (*Arabidopsis thaliana* nomenclature), in an AHASL protein can cause a sunflower plant expressing that protein to have enhanced resistance to a herbicide, particularly an IMI herbicide, a SU herbicide, a TP herbicide, a POB herbicide, and/or mixtures thereof. More specifically, this mutant protein confers multiple herbicide resistance on the plants.

Accordingly, the herbicide-resistant sunflower plants described herein include, but are not limited to, sunflower plants which have in their genomes at least one copy of an AHASL polynucleotide that encodes a herbicide-resistant AHASL protein having a leucine substitution at amino acid position 574 (*Arabidopsis thaliana* nomenclature). Furthermore, those of ordinary skill will recognize that such amino acid positions can vary depending on whether amino acids are added or removed from, for example, the N-terminal end of an amino acid sequence. Thus, embodiments of the present invention encompassed herein include amino acid substitutions at the recited position or equivalent position (e.g., "amino acid position 574 or equivalent position"). An "equivalent position" is a position that is within the same region as the exemplified amino acid position. Such regions are know in the art or can be determined by multiple sequence alignments as described herein or by methods known in the art.

A single amino acid substitution that can be used to produce herbicide-resistant sunflower AHASL proteins is provided together with the polynucleotides encoding such proteins, and herbicide-resistant plants, plant tissues, plant cells, and seeds carrying this mutation. Also provided are isolated sunflower AHASL1, AHASL2 and AHASL3 polynucleotides that encode herbicide-resistant AHASL1, AHASL2 and AHASL3 proteins, respectively. Such herbicide-resistant AHASL1, AHASL2 and AHASL3 proteins each comprise an amino acid other than tryptophan at position 574 or equivalent position (*Arabidopsis thaliana* nomenclature). Preferably in such herbicide-resistant AHASL1, AHASL2 and AHASL3 proteins, the amino acid at position 574 or equivalent position is leucine.

Further, isolated polypeptides encoding AHASL proteins are provided. The isolated polypeptides encode an amino acid sequence having the amino acid sequences set forth in FIG. 8 (amino acid sequence of the AHASL1 gene of the line RW-B, SEQ ID NO: 2), the amino acid sequences encoded by nucleotide sequences set forth in FIG. 7 (nucleotide sequence of the AHASL1 gene of the line RW-B, SEQ ID NO: 1), and functional fragments and variants of said amino acid sequences that encode an AHASL polypeptide comprising AHAS activity.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by AHAS activity assays. See, for example, Singh et al. (1988) Anal. Biochem. 171: 173-179, herein incorporated by reference. Additionally, the proteins described herein encompass both naturally occurring proteins as well as variations and modified forms thereof. Such variants will continue to possess the desired AHAS activity.

The invention also provides isolated or purified polynucleotides and proteins. An "isolated" or "purified" polynucleotide molecule or protein, or biologically active portion thereof, is substantially or essentially free from components that normally accompany or interact with the polynucleotide molecule or protein as found in its naturally occurring environment. Thus, an isolated or purified polynucleotide molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated polynucleotide molecule can contain less than about 5 kb, 4 kb, 3 kb, 2 kb, 1 kb, 0.5 kb, 0.4 kb, 0.3 kb, 0.2 kb or 0.1 kb of nucleotide sequences that naturally flank the polynucleotide molecule in genomic DNA of the cell from which the nucleic acid is derived. A protein that is substantially free of cellular material includes preparations of protein having less than about 30%, 25%, 20%, 15%, 10%, 9%, 8%, 7%, 6%, 5%, 4%, 3%, 2% or 1% (by dry weight) of contaminating protein. When the protein of the present invention or biologically active portion thereof is recombinantly produced, preferably culture medium represents less than about 30%, 25%, 20%, 15%, 10%, 9%, 8%, 7%, 6%, 5%, 4%, 3%, 2% or 1% (by dry weight) of chemical precursors or non-protein-of-interest chemicals.

Isolated polynucleotide molecules having nucleotide sequences that encode AHASL proteins and the corresponding proteins are provided. Also provided are nucleotide sequences encoding a herbicide-resistant AHASL protein from an herbicide-resistant sunflower plant. In one embodiment, the herbicide-resistant sunflower AHASL proteins have a tryptophan-to-leucine substitution at amino acid position 574 or equivalent position (*Arabidopsis thaliana* nomenclature) when compared to the corresponding wild-type amino acid sequence. In particular, isolated polynucleotide molecules are provided that comprise nucleotide sequences encoding the amino acid sequences shown in FIG. 8 and fragments and variants thereof that encode polypeptides comprising AHAS activity. Further provided are polypeptides having an amino acid sequence encoded by a polynucleotide molecule described herein, for example those set forth in FIG. 7, and fragments and variants thereof that encode polypeptides comprising AHAS activity.

In addition, the skilled artisan will further appreciate that changes can be introduced by mutation into the nucleotide sequences of the invention thereby leading to changes in the amino acid sequence of the encoded AHASL proteins without altering the biological activity of the AHASL proteins. Thus, an isolated polynucleotide molecule encoding an AHASL protein having a sequence that differs from that of SEQ ID NO: 2, can be created by introducing one or more nucleotide substitutions, additions, or deletions into the corresponding nucleotide sequence described herein, such that one or more amino acid substitutions, additions or deletions are introduced into the encoded protein. Mutations can be introduced by standard techniques, such as site-directed mutagenesis and PCR-mediated mutagenesis.

The isolated herbicide-resistant AHASL polynucleotide molecules of the invention can be used in polynucleotide constructs for the transformation of plants, particularly crop plants, to enhance the resistance of the plants to herbicides, particularly herbicides that are known to inhibit AHAS activity, more particularly an IMI herbicide, a SU herbicide, a TP herbicide, POB herbicide, and/or mixtures thereof. Such polynucleotide constructs can be used in expression cassettes, expression vectors, transformation vectors, plasmids and the like. The transgenic plants obtained following transformation with such polynucleotide constructs show increased resistance to AHAS-inhibiting herbicides such as, for example, an IMI herbicide, a SU herbicide, a TP herbicide, a POB herbicide, and/or mixtures thereof.

The isolated polynucleotide molecules having a nucleotide sequence that encodes a mutant AHASL protein as described above can be used in vectors to transform plants so that the plants created have enhanced resistant to herbicides, particularly an IMI herbicide, a SU herbicide, a TP herbicide, a POB herbicide, and/or mixtures thereof. The isolated AHASL polynucleotide molecules of the present invention can be used in vectors alone or in combination with a nucleotide sequence encoding the small subunit of the AHAS (AHASS) enzyme in conferring herbicide resistance in plants. See, U.S. Pat. No. 6,348,643, which is herein incorporated by reference.

Polynucleotide molecules that differ from the nucleotide sequences described herein are also encompassed by the present invention. The nucleotide sequences of the present invention include those sequences that encode the AHASL proteins described herein but that differ conservatively because of the degeneracy of the genetic code. These naturally occurring allelic variants can be identified with the use of well-known molecular biology techniques, such as polymerase chain reaction (PCR) and hybridization techniques as outlined below. The nucleotide sequences also include synthetically derived nucleotide sequences that have been generated, for example, by using site-directed mutagenesis but which still encode the AHASL protein. Generally, nucleotide sequence variants of the present invention will have at least about 70%, 75%, 80%, 85%, 90%, 91%, 92%, 93%, 94%, 95%, 96%, 97%, 98%, or 99% sequence identity to a particular nucleotide sequence described herein. The AHASL nucleotide sequence will encode an AHASL protein, respectively, that has an amino acid sequence having at least about 70%, 75%, 80%, 85%, 90%, 91%, 92%, 93%, 94%, 95%, 96%, 97%, 98%, or 99% sequence identity to the amino acid sequence of an AHASL protein described herein.

Embodiments of the invention also relates to a plant expression vector having a promoter that drives expression in a plant operably linked to an isolated polynucleotide molecule of the present invention. The isolated polynucleotide molecule comprises a nucleotide sequence encoding an AHASL protein, or a functional fragment and variant thereof. Plant expression vectors of the embodiments of the present invention do not depend on a particular promoter, only that such a promoter is capable of driving gene expression in a plant cell. Preferred promoters include constitutive promoters and tissue-preferred promoters.

The transformation vectors can be used to produce plants transformed with a gene of interest. The transformation vector will have a selectable marker gene of the present invention and a gene of interest to be introduced and typically expressed in the transformed plant. Such a selectable marker gene having a herbicide-resistant AHASL polynucleotide of the present invention operably linked to a promoter that drives expression in a host cell. For use in plants and plant cells, the transformation vector has a selectable marker gene comprising a herbicide-resistant AHASL polynucleotide of the present invention operably linked to a promoter that drives expression in a plant cell. The genes of interest of the present invention vary depending on the desired outcome. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment, the genes of interest include insect resistance genes such as, for example, Bacillus thuringiensis toxin protein genes (U.S. Pat. Nos. 5,366,892; 5,747,450; 5,736,514; 5,723,756; 5,593,881; and Geiser et al. (1986) Gene 48: 109). The AHASL proteins or polypeptides described herein can be purified from, for example, sunflower plants. Also, an isolated polynucleotide molecule encoding an AHASL protein of the present invention can be used to express an AHASL protein of the present invention in a microbe such as E. coli or a yeast. The expressed AHASL protein can be purified from extracts of E. coli or yeast by any method known to those of ordinary skill in the art.

Embodiments of the present invention encompasses AHASL polynucleotide molecules and fragments and variants thereof. For purposes of this invention, the term "fragments and variants" means fragments and variants of the exemplified polypeptides that comprise AHAS activity. In certain embodiments, the methods involve the use of herbicide-tolerant or herbicide-resistant plants. A fragment of an AHASL nucleotide sequence of the present invention may encode a biologically active portion of an AHASL protein, or it may be a fragment that can be used as a hybridization probe or PCR primer using methods described below. A biologically active portion of an AHASL protein can be prepared by isolating a portion of one of the AHASL nucleotide sequences of the present invention, expressing the encoded portion of the AHASL protein (e.g., by recombinant expression in vitro), and assessing the activity of the encoded portion of the AHASL1 protein. Polynucleotide molecules that are fragments of an AHASL nucleotide sequence comprise at least about 15, 20, 25, 30, 40, 50, 75, 100, 150, 200, 250, 300, 350, 400, 450, 500, 550, 600, 650, 700, 750, 800, 850, 900, 950, 1000, 1050, or 1100 nucleotides, or up to the number of nucleotides present in a full-length nucleotide sequence described herein depending upon the intended use.

A fragment of an AHASL nucleotide sequence that encodes a biologically active portion of an AHASL protein of the present invention will encode at least about 15, 20, 25, 30, 40, 50, 75, 100, 125, 150, 175, 200, 225, 250, 275, 300, 325 or 350 contiguous amino acids, or up to the total number of amino acids present in a full-length AHASL protein of the present invention. Fragments of an AHASL nucleotide sequence that are useful as hybridization probes for PCR primers need not encode a biologically active portion of an AHASL protein.

Variant AHASL nucleotide sequences can be made by introducing mutations randomly along all or part of an AHASL coding sequence, such as by saturation mutagenesis, and the resultant mutants can be screened for AHAS activity to identify mutants that retain AHAS activity, including herbicide-resistant AHAS activity. Following mutagenesis, the encoded protein can be expressed recombinantly, and the activity of the protein can be determined using standard assay techniques. Thus, the nucleotide sequences of the invention include the sequences described herein as well as fragments and variants thereof. The AHASL nucleotide sequences of the present invention, and fragments and variants thereof, can be used as probes and/or primers to identify and/or clone AHASL homologies in other plants, such probes can be used to detect transcripts or genomic sequences encoding the same or identical proteins. In this manner, methods such as PCR, hybridization, and the like can be used to identify such sequences having substantial identity to the sequences of the present invention. See, for example, Sambrook et al. (1989) Molecular Cloning: Laboratory Manual (2d ed., Cold Spring Harbor Laboratory Press, Plainview, N.Y.) and Innis, et al. (1990) PCR Protocols: A Guide to Methods and Applications (Academic Press, NY). AHASL nucleotide sequences isolated based on their sequence identity to the AHASL nucleotide sequences set forth herein or to fragments and variants thereof are encompassed by the present invention.

Transgenesis

Described herein are methods for creating a transgenic plant that is resistant to herbicides. The methods include transforming a plant with a plant expression vector having a promoter that drives expression in a plant that is operably linked to an isolated polynucleotide molecule of the invention. The isolated polynucleotide molecule having a nucleotide sequence encoding an AHASL protein or a functional fragment and variant of the amino acid sequences.

Embodiments of the present invention provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively.

The AHASL polynucleotides described herein are used in methods for enhancing the resistance of herbicide-tolerant plants. In one embodiment, the herbicide-tolerant plants have a herbicide-tolerant or herbicide-resistant AHASL protein. The herbicide-tolerant plants include both plants transformed with a herbicide-tolerant AHASL nucleotide sequences and plants that have in their genomes an endogenous gene that encodes a herbicide-tolerant AHASL protein. Nucleotide sequences encoding herbicide-tolerant AHASL proteins and herbicide-tolerant plants having an endogenous gene that encodes a herbicide-tolerant AHASL protein include the polynucleotides and plants described herein and those that are known in the art. See, for example, U.S. Pat. Nos. 5,013,659, 5,731,180, 5,767,361, 5,545,822, 5,736,629, 5,773,703, 5,773,704, 5,952,553 and 6,274,796; all of which are herein incorporated by reference. Such methods for enhancing the resistance of herbicide-tolerant plants comprise transforming a herbicide-tolerant plant with at least one polynucleotide construction having a promoter that drives expression in a plant cell that is operably linked to a herbicide-resistant AHASL polynucleotide of the invention, particularly the polynucleotide encoding a herbicide-resistant AHASL protein and fragments and variants said of polynucleotides that encode polypeptides comprising herbicide-resistant AHAS activity. None of the AHASL proteins prior to the present invention were capable, however, of conferring the broad spectrum and potent herbicide resistance obtained using the AHASL gene of the present invention.

Numerous plant transformation vectors and methods for transforming plants are available. See, for example, An, G. et al. (1986) Plant Physiol. 81:301-305; Fry, J., et al. (1987) Plant Cell Rep. 6:321-325; Block, M. (1988) Theor. Appl Genet. 76:767-77; Hinchee, et al. (1990) Stadler. Genet. Symp. 203212.203-212; Cousins, et al. (1991) Aust. J. Plant Physiol, 18:481-494; Chee, P. P. and Slightom, J. L. (1992) Gene 118:255-260; Christou, et al. (1992) Trends. Biotechnol. 10:239-246; D'Halluin, et al. (1992) Bio/Technol. 10:309-314; Dhir, et al. (1992) Plant Physiol. 99:81-88; Casas et al. (1993) Proc. Nat. Acad. Sci. USA 90:11212-11216; Christou, P. (1993) In Vitro Cell. Dev. Biol-Plant; 29P:119-124; Davies, et al. (1993) Plant Cell Rep. 12:180-183; Dong, J. A. and Mchughen, A. (1993) Plant Sci. 91: 139-148; Franklin, C. I. and Trieu, T. N. (1993) Plant Physiol. 102:167; Golovkin, et al. (1993) Plant Sci. 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al., (1994) Plant. J. 5:299-307; Borkowska et al. (1994) Acta. Physiol. Plant 16:225-230; Christou, P. (1994) Agro. Food. Md Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

Embodiments of the methods of the invention include introducing a polynucleotide construct into a plant. The term "introducing" means presenting to the plant the polynucleotide construct in such a manner that the construct gains access to the interior of a cell of the plant. The methods do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods. The term "stable transformation" means that the polynucleotide construct introduced into a plant integrates into the genome of the plant and is capable of being inherited by progeny thereof. The term "transient transformation" means that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the present invention, an AHASL nucleotide sequence is operably linked to a plant promoter that is known for high-level expression in a plant cell, and this construct is then introduced into a plant that is susceptible to one or more of the following herbicides, an IMI herbicide, a SU herbicide, a TP herbicide, or a POB herbicide, and a transformed plant is regenerated. The transformed plant is tolerant to exposure to a level of an IMI herbicide, a SU herbicide, a TP herbicide, a POB herbicide, and/or mixtures thereof that would kill or significantly injure an untransformed plant. This method can be applied to any plant species; however, it is preferably beneficial when applied to sunflower plants.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or micro projectile bombardment for direct DNA uptake. Such methods are known in the art. (U.S. Pat. No. 5,405,765 to Vasil et al.; Bilang et al. (1991) Gene 100: 247-250; Scheid et al., (1991) Mol. Gen. Genet., 228: 104-112; Gnerche et al., (1987) Plant Science 52: 111-116; Neuhause et al., (1987) Theor. Appl Genet. 75: 30-36; Klein et al., (19S7) Nature 327: 70-73; Howell et al. (1980) Science 208:1265; Horsch et al. (19S5) Science 227: 1229-1231; DeBlock et al. (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, Eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) Biotechniques 4:320-334, electroporation as described by Riggs et al. (1986) Proc. Natl. Acad. Sci. USA 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) EMBO J. 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Micro projectile Bombardment," in Plant Cell, Tissue, and Organ Culture: Fundamental Methods, ed. Gamborg and Phillips (Springer-Verlag, Berlin); McCabe et al. (1988) Biotechnology) 6:923-926); and Lecl transformation (WO 00/28058) See also; De Wet et al. (1985) in The Experimental Manipulation of Ovule Tissues, ed. Chapman et al. (Longman, New York), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4: 1495-1505 (electroporation); Li et al. (1993) Plant Cell Reports 12:250-255; all of which are herein incorporated by reference.

The polynucleotides of the embodiments of the present invention may be introduced into plants by contacting plants with a virus or viral nucleic acids. Generally, such methods involve incorporating a polynucleotide construct of the present invention within a viral DNA or RNA molecule. It is recognized that the an AHASL protein of the present invention may be initially synthesized as part of a viral polyprotein, which later may be processed by proteolysis in vivo or in vitro to produce the desired recombinant protein. Further, it is recognized that promoters of the present invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments of the present invention provide a transformed seed (also referred to as "transgenic seed") having a polynucleotide construct of the present invention, for example, an expression cassette of the present invention, stably incorporated into their genome. The herbicide-resistant plants described herein find use in methods for controlling weeds. Thus, the embodiments of the invention include methods for controlling weeds in the vicinity of a herbicide-resistant plant of the present invention. The methods comprise applying an effective amount of a herbicide to the weeds and to the herbicide-resistant plant, wherein the plant has increased resistance to one or more of the following herbicides, an IMI herbicide, a SU herbicide, a TP herbicide, a POB herbicide, and/or mixtures thereof, when compared to a wild-type plant.

Embodiments of the present invention provide non-transgenic and transgenic seeds with increased tolerance to one or more herbicide, particularly an AHAS-inhibiting herbicide, more particularly an IMI herbicide, a SU herbicide, a TP herbicide, a POB herbicide, and/or mixtures thereof. Such seeds include, for example, non-transgenic sunflower seeds comprising the herbicide-tolerance characteristics of the sunflower plant RW-B, and transgenic seeds comprising a polynucleotide molecule of the present invention that encodes a herbicide-resistant AHASL protein.

Testing for Presence of the Mutant AHASL Gene

The nucleotide sequences of the embodiments of the present invention can be used to isolate corresponding sequences from other organisms, particularly other plants, more particularly other dicots. In this manner, methods such as PCR, hybridization, and the like can be used to identify such sequences based on their sequence homology to the sequences set forth herein. Sequences isolated based on their sequence identity to the entire AHASL polynucleotide sequences set forth herein or to fragments thereof are encompassed by the present invention. Thus, isolated polynucleotide sequences that encode for an AHASL protein and which hybridize under stringent conditions to the sequences described herein, or to fragments thereof, are included in the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like. The AHASL polynucleotide sequences of the present invention are provided in expression cassettes for expression in the plant of interest. The cassette will include 5' and 3' regulatory sequences operably linked to an AHASL polynucleotide sequence of the present invention. "Operably linked" is a functional linkage between a promoter and a second sequence, where the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the AHASL polynucleotide sequence to be under the transcriptional regulation of the regulatory regions. The expression cassette may additionally contain selectable marker genes. The expression cassette will include in the 5'-3' direction of transcription, a transcriptional and translational initiation region (i.e., a promoter), an AHASL polynucleotide sequence of the present invention, and a transcriptional and translational termination region (i.e., termination region) functional in plants. The promoter may be native or analogous, or foreign or heterologous, to the plant host and/or to the AHASL polynucleotide sequences of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the AHASL polynucleotide sequence, it is intended that the promoter is not the native or naturally occurring promoter for the operably linked AHASL polynucleotide sequence. As used herein, a chimeric gene comprises a coding sequence operably linked to a transcription initiation region that is heterologous to the coding sequence.

While the herbicide-resistant AHASL polynucleotides described herein can be used as selectable marker genes for plant transformation, the expression cassettes containing these polynucleotides can include another selectable marker gene for the selection of transformed cells. Selectable marker genes, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal 5 compounds, such as glufosinate ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 1:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 10 49:603-612; Figge et al. (1988) Cell 52:713-722; Deuschle et al. (1989) Proc. Natl. Acad. Sci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90: 1917-1921; Labow et al. (1990) Mol. Cell. Biol. 10:3343-3356; Zambretti et al. (1992) Proc. Natl. Acad. Sci. USA 15 89:3952-3956; Baim et al. (1991) Proc. Natl. Acad, Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschr M et al. (1988) Biochemistry 27: 1094-1104; Bonin (1993) PhD. Thesis, University of Heidelberg; Gossen et al. (1992) Proc. Natl. Acad Sci. USA 89:5547-5551; Oliva et al. (1992) Antimicrob. Agents Chemother. 36:913-919; Hlavka et al. (1985) Handbook of Experimental Pharmacology, Vol. 78 (Springer- Verlag, Berlin); Gill et al. (1988) Nature 334:721-724. Such present inventions are herein incorporated by reference. The above list of selectable marker genes is not meant to be limiting and any selectable marker gene can be used as required.

In a hybridization method, all or part of a known AHASL nucleotide sequence can be used to screen cDNA or genomic libraries. Methods for construction of such cDNA and genomic libraries are generally known in the art. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known AHASL nucleotide sequence described herein. Degenerate primers designed on the basis of conserved nucleotides or amino acid residues in a known AHASL nucleotide sequence or encoded amino acid sequence additionally can be used. The probe typically comprises a region of nucleotide sequence that hybridizes under stringent conditions to at least about 12, preferably about 25, more preferably about 50, 75, 100, 125, 150, 175, 200, 250, 300, 350, 400, 500, 600, 700, 800, 900, 1000, 1100, or more consecutive nucleotides of an AHASL nucleotide sequence of the present invention or a fragment or variant thereof. Preparation of probes for hybridization is generally known in the art.

For example, the entire AHASL sequence described herein, or one or more portions thereof, may be used as a probe capable of specifically hybridizing to corresponding AHASL sequences and messenger RNAs. Hybridization techniques include hybridization screening of plated DNA libraries (either plaques or colonies). Hybridization of such sequences may be carried out under stringent conditions. The terms "stringent conditions" or "stringent hybridization conditions" mean, for purposes of this invention, conditions under which a probe will hybridize to its target sequence to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York).

Transgenesis and Optimization of Expression

Methods for enhancing AHAS activity in a plant by transforming a plant with a polynucleotide construct having a promoter operably linked to an AHASL1 nucleotide sequence of the present invention are provided. The methods involve introducing a polynucleotide construct of the invention into at least one plant cell and regenerating a transformed plant using a promoter capable of driving gene expression in a plant cell. Preferably, such a promoter is a constitutive promoter or a tissue-preferred promoter. The methods find use in increasing the resistance or tolerance of a plant to at least one herbicide, and advantageously two, three, or four or more herbicides that interfere with the catalytic activity of the AHAS enzyme, particularly an IMI herbicide, a SU herbicide, a TP herbicide, a POB herbicide, and/or mixtures thereof.

Where appropriate, the gene(s) may be optimized for increased expression in the transformed plant. That is, the genes can be synthesized using plant-preferred codons for improved expression. See, for example, Campbell and Gowri (1990) Plant Physiol 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Nucleotide sequences for enhancing gene expression can also be used in the plant expression vectors. These include the introns of the maize Adhl, intronl gene (Callis et al. Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 describe the use of specific introns in gene expression constructs, and Gallie et al. (Plant Physiol. 106:929-939, 1994) also have shown that introns are useful for regulating gene expression on a tissue specific basis. To further enhance or to optimize AHAS large subunit gene expression, the plant expression vectors of the present invention may also contain DNA sequences containing matrix attachment regions (MARs). Plant cells transformed with such modified expression systems, then, may exhibit overexpression or constitutive expression of a nucleotide sequence of the present invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance translation can also be utilized, for example, introns, and the like. In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Expression cassettes for expressing polynucleotides in plants, plant tissues, plant cells, and other host cells are provided. The expression cassettes have a promoter expressible in the plant, plant tissue, plant cell, or other host cells of interest operably linked to a polynucleotide of the invention that has a nucleotide sequence encoding either a full-length (i.e. including the chloroplast transit peptide) or mature AHASL protein (i.e. without the chloroplast transit peptide). If expression is desired in the plastids or chloroplasts of plants or plant cells, the expression cassette may also have an operably linked chloroplast-targeting sequence that encodes a chloroplast transit peptide. Such expression cassettes can be used in a method for enhancing the herbicide tolerance of a plant or a host cell. The method involves transforming the plant or host cell with an expression cassette containing a promoter that is expressible in the plant or host cell of interest and the promoter is operably linked to a polynucleotide of an embodiment of the present invention that comprises a nucleotide sequence encoding, for example, an IMI herbicide, a SU herbicide, a TP herbicide, or a POB herbicide resistant AHASL protein.

The use of the term "polynucleotide constructs" is not limited to DNA. Those of ordinary skill in the art will recognize that polynucleotide constructs, particularly polynucleotides and oligonucleotides, comprised of ribonucleotides and combinations of ribonucleotides and deoxyribonucleotides may also be employed in the methods described herein. Such deoxyribonucleotides and ribonucleotides include both naturally occurring molecules and synthetic analogues. The polynucleotide constructs of the invention also encompass all forms of polynucleotide constructs including, but not limited to, single-stranded forms, double-stranded forms, hairpins, stem-and-loop structures, and the like. Furthermore, it is understood by those of ordinary skill in the art that each nucleotide sequence described herein also includes the complement of that exemplified nucleotide sequence.

The methods of the invention may employ a polynucleotide construct that is capable of directing, in a transformed plant, the expression of at least one protein, or at least one RNA, such as, for example, an antisense RNA that is complementary to at least a portion of an mRNA. Typically such a polynucleotide construct is comprised of a coding sequence for a protein or an RNA operably linked to 5' and 3' transcriptional regulatory regions. Alternatively, a polynucleotide construct may be used that is not capable of directing, in a transformed plant, the expression of a protein or an RNA. For expression of a polynucleotide of the present invention in a host cell of interest, the polynucleotide typically is operably linked to a promoter that is capable of driving gene expression in the host cell of interest. The methods for expressing the polynucleotides in host cells do not depend on particular promoter, and include the use of any promoter that is known in the art and that is capable of driving gene expression in the host cell of interest.

While it may be preferable to express AHASL polynucleotides using heterologous promoters, the native promoter sequences may be used. Such constructs would change expression levels of the AHASL protein in the plant or plant cell. Thus, the phenotype of the plant or plant cell is altered. The termination region may be native with the transcriptional initiation region, may be native with the operably linked AHASL sequence of interest, may be native with the plant host, or may be derived from another source (i.e., foreign or heterologous to the promoter, the AHASL polynucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5: 141-149; Mogen et al. (1990) Plant Cell 2: 1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

A number of promoters can be used in the practice of the invention and can be selected based on the desired outcome. The nucleic acids can be combined with constitutive, tissue-preferred, or other promoters for plant expression. Such constitutive promoters include, for example, the core promoter of the Rsyn7 promoter and other constitutive promoters described in WO 99/43838 and U.S. Pat. No. 6,072,050; the core CaMV 35S promoter (Odell et al. (1985) Nature 313: 810-812); rice actin (McElroy et al. (1990) Plant Cell 2: 163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. Tissue-preferred promoters can be utilized to target enhanced AHASL expression within a particular plant tissue. Such tissue-preferred promoters include, but are not limited to, leaf-preferred promoters, root-preferred promoters, seed-preferred promoters, and stem-preferred promoters. Tissue-preferred promoters, are described in, for example, Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Prob I. Cell Differ. 20:181-196; Orozco et al. (1993) Plant Mol. Biol. 23(6): 1129-1138; Matsuoka et al. (1993) Proc. Natl. Acad. Sci. USA 90(20):9586-9590; and Guevara-Garcia et al. (1993) Plant J. 4(3):495-505. Such promoters can be modified, if necessary, for weak expression.

In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the AHASL polynucleotide such that the two sequences are contiguous and in the same reading frame. See, for example, Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

While the AHASL proteins described herein can include a native chloroplast transit peptide, any chloroplast transit peptide known in the art can be fused to the amino acid sequence of a mature AHASL protein of the present invention by operably linking a chloroplast-targeting sequence to the 5'-end of a nucleotide sequence encoding a mature AHASL protein.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) (Archer et al. (1990) J Bioenerg. Biomemb. 22(6):789-810); tryptophan synthase (Zhao et al. (1995) J. Biol. Chem. 270(11):6081-6087); plastocyanin (Lawrence et al. (1997) J. Biol. Chem. 272(33):20357-20363); chorismate synthase (Schmidt et al. (1993) J. Biol. Chem. 268(36):27447-27457); and the light harvesting chlorophyll a/b binding protein (LHBP) (Lamppa et al. (1988) J. Biol. Chem. 263:14996-14999). See also Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84:965-968; Romer et al. (1993) Biochem. Biophys. Res. Commun. 196: 1414-1421; and Shah et al. (1986) Science 233:478-481.

Methods for transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

As described herein, the AHASL nucleotide sequences of the embodiments of the present invention find use in enhancing the herbicide tolerance of plants that comprise in their genomes a gene encoding a herbicide-tolerant AHASL protein. Such a gene may be an endogenous gene or a transgene. Additionally, in certain embodiments, the nucleic acid sequences of the present invention can be stacked with any combination of polynucleotide sequences of interest in order to create plants with a desired phenotype. For example, the polynucleotides may be stacked with any other polynucleotides encoding polypeptides having pesticidal and/or insecticidal activity, such as, for example, the Bacillus thuringiensis toxin proteins (described in U.S. Pat. Nos. 5,366,892; 5,747,450; 5,737,514; 5,723,756; 5,593,881; and Geiser et al. (1986) Gene 48:109). The combinations generated can also include multiple copies of any one of the polynucleotides of interest.

The nucleotide sequences described herein may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Further provided are methods for increasing the herbicide-resistance of a sunflower plant through conventional plant breeding involving sexual reproduction. The methods comprise crossing a first sunflower plant that is resistant to a herbicide to a second sunflower plant that may or may not be resistant to the herbicide or may be resistant to different herbicide or herbicides than the first plant. The first plant can be any of the herbicide resistant plants described herein including, for example, RW-B. The second plant can be any plant that is capable of producing viable progeny plants (i.e., seeds) when crossed with the first plant. Typically, but not necessarily, the first and second plants are of the same species of sunflower. The progeny plants produced by this method have increased resistance to a herbicide when compared to either the first or second plant or both. When the first and second plants are resistant to different herbicides, the progeny plants will have the combined herbicide tolerance characteristics of the first and second plants. These methods can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. Further, these methods can additionally involve selecting plants that comprise the herbicide tolerance characteristics of the first plant, the second plant, or both the first and the second plant.

Methods of Weed Control

Sunflower crops are often rotated with cereals, such as wheat. SU herbicides are often employed as part of the wheat weed control system. In addition to SU herbicides, IMI herbicides can be used as part of the wheat weed control system when growing IMI wheats. The use of these herbicides in a wheat/sunflower rotation leads to carryover damage. Sunflower herbicide carryover damage occurs when residues of a herbicide applied to the previous crop, in this example SU or IMI applied to wheat, are present in the soil when a sunflower crop is planted. Indeed, several herbicides can cause carryover damage to sunflower, including many AHAS-inhibitors (Blamey et al., 1997). The damage to sunflower crops can be reduced by using herbicide resistant sunflower cultivars.

Herbicide resistant sunflower cultivars, however, show great specificity and their use only permits spraying the same family of herbicide in post-emergence. For example, in order to protect a sunflower crop from SU carryover, SU-resistant cultivars can be used. The use of SU-resistant cultivars allows only SU herbicides to be sprayed over the sunflower crop. At present, only SU-resistant or IMI-resistant specific cultivars have been shown—no cultivars have been described showing cross-resistance to different AHAS-inhibitors. Surprisingly, and unexpectedly, the presence of the gene described herein and expression of the corresponding AHAS protein protects sunflower crops from potential carryover damage caused by AHAS-inhibitor herbicides and subsequently, allows the spraying of a variety of AHAS-inhibitor herbicides to control weeds in post emergence. This ability to use a variety of herbicides for weed control in a sunflower crop provides greatly enhanced opportunity for growers to control weed infestation in sunflower crops.

The surprising discovery of an AHAS protein having resistance to multiple herbicides allows for:

1. The possibility to apply new types of AHAS-inhibiting herbicides for weed control in the sunflower crop (i.e.: POBs and TPs) or the registration in sunflower of well known herbicides used in another crops.

2. The mixing of two or more of the herbicides for application at the same time on the sunflower crop because of the high levels of cross-resistance to different families of AHAS-inhibitor herbicides. Additionally, the cross-resistance allows for designing and developing new herbicide formulations which can combine different AHAS-inhibitor herbicides with the aim of increasing weed spectrum control in sunflower.

3. Greater flexibility in herbicide management for weed control in sunflower, that is, more than one type of herbicide can be chosen and applied at different times in the same season depending on the type of weed to be controlled.

4. Resistance to the herbicide carryover from the previous crop and, at the same time, resistance to another AHAS-inhibitor herbicide applied in post-emergence.

The control of undesired vegetation is understood as meaning the killing of weeds and/or otherwise retarding or inhibiting the normal growth of the weeds. Weeds, in the broadest sense, are understood as meaning all those plants which grow in locations where they are undesired. Examples of weeds include but are not limited to, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*.

In addition, the weeds can include, for example, crop plants that are growing in an undesired location. For example, a volunteer maize plant that is in a field that predominantly having sunflower plants can be considered a weed, if the maize plant is undesired in the field of sunflower plants.

Embodiments of the present invention describes methods for increasing the tolerance or resistance of a plant, plant tissue, plant cell, or other host cell to one or more herbicide that interferes with the activity of the AHAS enzyme. Preferably, such a herbicide is an IMI herbicide, a SU herbicide, a TP herbicide, a POB herbicide, and/or mixtures thereof. Advantageously increased resistance or tolerance to two or more of the above herbicides. More advantageously, increased resistance or tolerance to three or more of the above herbicides. Most advantageously, increased resistance or tolerance to four or more of the above herbicides. The IMI herbicides can include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). The IMI herbicide can be selected from, but is not limited to, 2-(4-isopropyl-4-methyl-5-oxo-2-imidiazolin-2-yl)-nicotinic acid, [2-(4-isopropyl)-4-J bmethyl-5-oxo-2-imidazolin-2-yl)-3-quinolinecarboxylic]acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-J imidazolin-2-yl)-5-methylnicotinic acid, and a mixture of methyl [6-(4-isopropyl-4-]methyl-5-oxo-2-imidazolin-2-yl)-m-toluate and methyl [2-(4-isopropyl-4-methyl-5-]oxo-2-imidazolin-2-yl)-p-toluate. The use of 5-ethyl-2-(4-isopropyl-4-methyl-5-oxo-2-imidazolin-2-yl)-nicotinic acid and [2-(4-isopropyl-4-methyl-5-oxo-2-imidazolin-2-]yl)-5-(methoxymethyl)-nicotinic acid is preferred. The use of [2-(4-isopropyl-4-]methyl-5-oxo-2-imidazolin-2~yl)-5-(methoxymethyl)-nicotinic acid is particularly preferred.

The SU herbicides can include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, derivatives of any of the aforementioned herbicides, and a mixture of two or more of the aforementioned herbicides.

The TP herbicides can include, but are not limited to, cloransulam, diclosulam, florasulam, flumetsulam, metosulam, and penoxsulam.

The POB herbicides can include, but are not limited to, bispyribac, pyrithiobac, pyriminobac, pyribenzoxim and pyriftalid.

It is recognized that POB herbicides are closely related to the pyrimidinylthiobenzoate herbicides and are generalized under the heading of the latter name by the Weed Science Society of America. Accordingly, the herbicides can include pyrimidinylthiobenzoate herbicides, including, but not limited to, the POB herbicides described above. In light of the above, Applicants use the terms pyrimidinylthiobenzoate and pyrimidinyloxybenzoate interchangeably with the abbreviation POB.

The use of the herbicides listed herein is not intended to limit the present invention to a specific herbicide or specific family of herbicides. Those of ordinary skill in the art will recognize that other herbicides may also be employed.

By providing plants having increased resistance to herbicides a wide variety of formulations can be employed for protecting sunflower plants from weeds, so as to enhance sunflower plant growth and reduce competition for nutrients. A herbicide can be used by itself for pre-emergence, post-emergence, pre-planting and at planting control of weeds in areas surrounding the plants described herein. In an embodiment, an IMI herbicide formulation can be used that contains other additives. In another embodiment, a SU herbicide formulation can be used that contains other additives. In another embodiment, a TP herbicide formulation can be used that contains other additives. In another embodiment, a POB herbicide formulation can be used that contains other additives. The herbicide(s) can also be used as a seed treatment. Additives found in formulations of an IMI herbicide, a SU herbicide, a TP herbicide, a POB herbicide and/or mixtures thereof can include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, or the like. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid diethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates). Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation. Suitable antifoaming agents are for example antifoaming agents based on silicon or magnesium stearate.

Suitable preservatives are for example Dichlorophen and enzylalkoholhemiformal. Sunflower seed treatment formulations may additionally comprise binders and optionally colorants. Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), poly ethers, polyurethans, polyvinylacetate, tylose and copolymers derived from these polymers.

Optionally, colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a suitable gelling agent is carrageen (Satiagel®). Powders, materials for spreading, and dustable products can be prepared by mixing or concomitantly grinding the active substances with a solid carrier. Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the AHAS-inhibiting herbicide. In this case, the AHAS-inhibiting herbicides are employed in a purity of from 90% to 100% by weight, preferably 95% to 100% by weight (according to NIVIR spectrum). For sunflower seed treatment purposes, respective formulations can be diluted 2-10 fold leading to concentrations in the ready to use preparations of 0.01 to 60% by weight active compound by weight, preferably 0.1 to 40% by weight.

The AHAS-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the present invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

In one embodiment of the present invention, a further subject of the present invention is a method of treating soil by the application, in particular into the seed drill: either of a granular formulation containing the AHAS-inhibiting herbicide as a composition/formulation (e.g. a granular formulation, with optionally one or more solid or liquid, agriculturally acceptable carriers and/or optionally with one or more agriculturally acceptable surfactants. This method is advantageously employed in seedbeds of sunflowers.

Embodiments of the present invention also describes sunflower seeds coated with and/or containing a seed treatment formulation comprising at least one AHAS-inhibiting herbicide selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means, in a preferred embodiment, true seeds.

The term "coated with and/or containing" generally signifies that the active ingredient is for the most part on the surface of the propagation product at the time of application, although a greater or lesser part of the ingredient may penetrate into the propagation product, depending on the method of application. When the propagation product is (re)planted, it may absorb the active ingredient.

The sunflower seed treatment application with the AHAS-inhibiting herbicide or with a formulation comprising the AHAS-inhibiting herbicide is carried out by spraying or dusting the seeds before sowing of the plants and before emergence of the plants.

In the treatment of sunflower seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the active ingredient ("a.i.") (or of the mixture of a.i. or of the formulation) per 100 kg of seed, preferably from 1 g to 5 kg per 100 kg of seed, in particular from 1 g to 2.5 kg per 100 kg of seed.

The following examples are offered by way of illustration and not by way of limitation.

Identification of Resistant Plants 300 seeds of a wild sunflower population known to be tolerant to IMIs were sown under greenhouse conditions at Nidera Experimental Station in Venado Tuerto, Santa Fe, Argentina, together with the control lines HA89, B770 (Susceptible—"5"), BTI-M1 and RHA426 (Resistant—"R"). At the V4 stage all the plants were sprayed with imazapyr at a rate of 80 gr ai/ha. Two weeks after treatment, all the plants were evaluated by visual inspection for injury. S lines HA89 and B770 were killed by the treatment. R line RHA426 showed signs of chlorosis and R line BTI-M1 did not present any signs of damage. In total, 159 plants of the wild population resisted the herbicide treatment and 129 were killed (categorized as S). Further, 18 of the 159 plants which survived the herbicide treatment showed no symptoms of herbicide injury, similar to the mutant R line BTI-M1, and were categorized as R.

Genetics of Resistance

One R plant (RW-73) was used as male in crosses with the cultivated susceptible lines HA89 and B770. Ten to 20 F1 plants from each cross were sprayed with imazapyr at a rate of 80 gr ai/ha, using B770 (S) and BTI-M1 (R) as controls. None of the F1 plants showed symptoms of herbicide injury, which was similar to the BTI-M1 plants. However, imazapyr treatment killed the B770 plants.

One F1 plant from the cross HA89/RW-73 was backcrossed to the susceptible parent. Also, one plant from the cross B770/RW-73 was backcrossed to B770. F2 seeds were obtained by pollinating F1 plants among them.

The BC1F1 and F2 seeds obtained were sown under greenhouse conditions together with B770 and BTI-M1, used as susceptible and resistant controls, respectively. At V3-V4 stage all the plants were sprayed with imazapyr at a rate of 80 gr ai/ha. Plants were scored 14 days after treatment as either R, S or I (intermediate). Plants were categorized as R if they showed no herbicide damage, S if they died or I if they displayed height reduction or chlorosis. Results of the inheritance of imidazolinone resistance in RW-73 are shown in FIG. 3.

In particular, FIG. 3 shows the response of sunflower plants [Resistant (R), Intermediate (I), Susceptible (S)] to imazapyr applied at a rate of 80 g a.i.ha$^{-1}$ in $F_1$, $F_2$ and $BC_1F_1$ populations resulting from crosses between resistant line, RW-73, and one of either two susceptible lines, B770 and HA89, and Chi-square tests of single locus model for control of resistance.

F2 populations resulting from susceptible x resistant crosses showed a good fit to a 1:2:1 R:I:S ratio, indicating segregation of a single gene for resistance to imazapyr. To confirm these results from the F2 populations, F1 plants were test crossed to the susceptible parents and the resulting progeny were evaluated for reaction to imazapyr. BC1F1 populations gave a good fit to a 1:1 I:S ratio, confirming the single locus hypothesis (Table 1).

The results of the genetic study indicate that resistance in RW-73 is inherited as a partially dominant trait conferred by a single nuclear-encoded gene. This pattern of inheritance is consistent with other findings that have reported the genetic control of resistance to AHAS inhibiting herbicides.

Development of a Sunflower Line that is Homozygous for the Herbicide Resistance Characteristic of RW-73

The heterogeneous and heterozygous condition of the wild sunflower population analyzed above precludes its use for relative level of resistance comparisons with respect to cultivated lines carrying herbicide-resistance traits. Using marker assisted backcrossing, a resistant line closely resembling B770 was developed which was coded RW-B. RW-B was homozygous for the resistance gene since its progeny obtained by selfing did not segregate for susceptibility after imazapyr application.

Resistance of RW-B to Different AHAS-Inhibitors Herbicides

Sunflower lines: The following genetic sunflower lines were used in determining AHAS resistance: two S lines ("B770" and "HA89"), two lines resistant to SUs derived from the population SURES (SuBL and SuRL), two lines resistant to IMIs derived from the population IMISUN ("Rha 426" and "B770imi") and the line "RW-B". HA89 and Rha426 are public inbred lines released by the USDA. SURES and IMISUN are breeding populations release by the USDA. B770 is a proprietary line from Nidera. B770imi is a proprietary line with B770 background carrying the resistant gene Imr1. RW-B was obtained as described above.

Method: Eight seeds from each of the seven lines were sown in 20-by-20-by-30 cm pots. After emergence, plantlets were thinned by hand leaving 4 plantlets per pot. Five pots of each line were treated with a different herbicide or dose. An untreated control pot of each line was included in each experiment. Plants were grown in a greenhouse under natural light conditions supplemented with 400 W halide lamps to provide a 14 h day length. Day/night temperatures were 25 and 20° C., respectively. At V4 stage of development (Schneiter and Miller 1981) plants were sprayed with three SU herbicides (Chlorsulfuron, Nicosulfuron and Foramsulfuron), three IMIs (Imazamox, Imazapyr and Imazapic), a POB (Bispyribac-Na) and a TP (Cloransulam-methyl). Fourteen days after treatment plants were scored phenotypically using a Phytotoxicity Index (PI). PI is a phenotypic scale from 0 to 9 that was assessed for each pot by visual inspection. Plants without any symptoms were recorded as "0," increasing levels of stunting and yellowing with respect to the untreated control plants were recorded as "1" to "4," increasing levels of leaf abnormalities and leaf necrosis were recorded from "5" to "8," and dead plants with total necrosis of the apex were recorded as "9." PI data for each experiment were analyzed by an ANOVA test, means were compared by a LSD test.

The results are shown in FIG. 4, which shows the phytotoxicity index of seven sunflower lines sprayed with different AHAS-inhibiting herbicides. Response of sunflower lines (B770, HA89, SuBL, SuRL, Rha426, B770imi and RW-B) to four different families of AHAS inhibiting herbicides. Data is presented MS among lines mean sum square, ***P<0.001, LSD least significant difference value. Mean values with the same letter indicate that they are not statistically different (P<0.01). The injury was measured using Phytotoxicity Index (PI).

The S lines HA89 and B770 were killed by all herbicide applications. The SU-resistant lines SuBL and SuRL were resistant to the three SUs used, but were killed by all the other herbicides. The IMI-resistant lines Rha426 and B770imi were moderately resistant to the three IMIs and were highly susceptible to the SUs, the POB and the TP. Remarkably, RW-B, showed high levels of resistance to all four families of herbicides. Surprisingly, the RW-B line showed the same level of resistance to SUs as the SU-resistant lines SuBL and SuRL and a better level of resistance to IMIs than the IMI-Resistant lines Rha426 and B770imi. Further, in another surprising result, RW-B showed a high level of resistance to a POB and a TP. None other lines showed this type of resistance.

Allelism Test

RW-B plants were crossed with RHA426 in order to determine if the resistant gene in RW-B is allelic to Imr1, the mutation previously described in imidazolinone resistant inbred lines. In this cross, $F_1$ hybrids plants were self pollinated and backcrossed to RHA426 to obtain the $F_2$ and $BC_1F_1$ generations, respectively. Plants from the parents and from $F_1$, $F_2$ and BC were challenged with 160 g a.i. ha$^{-1}$ and 320 g a.i. ha$^{-1}$ of imazapyr at the V2-V4 stage. Post challenge, plants were scored as described above. No susceptible plants were observed in the $F_2$ and BC populations resulting from this cross when progeny were evaluated at the lower herbicide rate, indicating that the resistance genes in RW-B and RHA426 are alleles of the same locus. These results are shown in FIG. 5. In particular, FIG. 5 shows the response of sunflower plants (i.e., as Resistant (R) and Susceptible (S)) to imazapyr applied at rates of 80 g a.i.ha-1 and 320 g a.i.ha-1 in F1, F2 and BC1F1 generations resulting from crosses between RW-B and the inbred line carrying the imidazolinone resistance gene Imrl, RHA 426.

On the other hand, when $F_2$ and BC populations were scored after applying herbicide at the higher rate (320 g a.i. ha$^{-1}$), segregation for susceptibility could be observed. Only two phenotypic classes were detected, a resistant class composed of plants that were without any sign of injury or only slight symptoms, and a susceptible phenotype that was killed at this dose in much the same way as the control line RHA426. The observed segregation ratios over 508 $F_2$ plants screened were not significantly different from a 3:1 segregation ratio (see Table 3). To confirm these results, $F_1$ plants were backcrossed to RHA426 and the resulting $BC_1F_1$ plants were screened at 320 g a.i. ha$^{-1}$ of imazapyr. Observed segregation ratios gave a good fit to a 1:1 R:S ratio, confirming that the resistant gene in RW-B showed complete dominance over the resistant gene in RHA426, and that both of the resistant genes are alleles of the same locus, AHAS1.

AHAS1 Haplotype Cosegregation with Herbicide Resistance

Materials and Methods: DNA was isolated from young leaves of lines B770, RW-B and RHA426 as well as from individual $F_1$ and $F_2$ plants from the cross RW-B/RHA426 using the method of Dellaporta (1983). AHAS1 gene fragments were PCR amplified using the primers p-AHAS18 and p-AHAS19 (Kolkman et al., 2004). PCR products were amplified in a 15-µl reaction containing 1 U Taq DNA Polymerase (Biotools), 70 ng genomic sunflower DNA, 25 µg Bovine serum albumin (BSA), with a final concentration of 100 µM of each dNTP, 0.25 µM of each primer, 90 mM Tris-HCl pH 8, 20 mM $(NH_4)_2SO_4$ and 2.5 mM $MgCl_2$. The PCR program consisted of an initial denaturation step at 94° C. for 2 min, followed by 40 cycles of 30 s at 94° C., 30 s at 56° C. and 30 s at 72° C., followed by a final elongation step at 72° C. for 10 min. Amplification products (3 µL/lane) were separated on a standard sequencing gel containing 6% polyacrylamide, 8 M urea, and 1×TBE, at 60 W constant power for 2 to 3 h, and were detected by silver nitrate staining (Silver Sequence™ Promega Biotech, USA). The size of each SSR allele was estimated using a molecular weight marker and a standard sequencing reaction in adjacent lanes of the gel.

Results: the AHAS1 gene in sunflower presents a simple sequence repeat (SSR) polymorphism which permits the discrimination of the lines carrying the Imr1 allele from any other sunflower genotype (Kolkman et al., 2004). PCR amplification of the AHAS1 gene fragment containing this SSR using the primers p-AHAS18 and p-AHAS19 yielded a product of 321 bp for RW-B and a fragment of 312 bp for RHA426. This length variant polymorphism detected in RW-B and RHA426 was exploited to investigate the segregation in the $F_2$ and $BC_1F_1$ populations derived from crossing both lines. One hundred and eleven plants from the $F_2$ population and 126 plants from the $BC_1F_1$ population were chosen at random, sampled for DNA isolation, challenged with an imazapyr application rate of 320 g a.i. ha$^{-1}$ and genotyped using this marker. In the $F_2$ population, 30 plants were killed by the herbicide (S) and 81 showed no symptoms or a slight injury (R). These data are shown in FIG. 6. In particular, FIG. 6 shows the reaction of sunflower plants (i.e., as Resistant (R) and Susceptible (S)) to imazapyr applied at a rate of 320 g a.i. ha-1 and AHAS1 haplotype segregation (A=RW-B haplotype, B=RHA426 haplotype) in F2 and BC1F1 population derived from the cross RW-B/RHA426.

The observed segregation ratio for resistance was not significantly different from the expected segregation ratio for a completely dominant factor segregating in $F_2$ (3R:1S). Observed segregation for the AHAS1 SSR marker (26 A/A: 55 A/B: 30 B/B) fits an expected segregation ratio for a codominant marker segregating in $F_2$ (1:2:1). All the susceptible plants genotyped for the AHAS1 SSR were homozygous for the RHA426 haplotype (B/B), whereas R-plants were either heterozygous (A/B) or homozygous for the RW-B haplotype (A/A) (see FIG. 6). The cosegregation of herbicide resistance phenotypes and AHAS1 haplotypes was further assessed on 126 $BC_1F_1$ progeny segregating for resistance. Observed segregation ratios for resistance fit a 1:1 ratio as expected for the segregation of one locus in $BC_1F_1$. AHAS1 SSR haplotypes completely cosegregated with phenotypes for herbicide reaction, 64 A/B: 62 B/B. Susceptible progeny were homozygous for the RHA426 haplotype (B/B), whereas resistant progeny were heterozygous for RHA426 and RW-B haplotypes (A/B). These results confirm that the resistant gene in RW-B is different from the resistance gene in RHA426 and that both of the genes are allelic variants of the locus AHAS1.

PCR Amplification and Sequencing of Sunflower AHAS1 Gene from RW-B

Genomic DNA was extracted from sunflower leaf tissue using Qiagen's DNeasy 96 Plant kit (catalog no. 69181). The AHASI gene was PCR amplified in three fragments and direct-sequenced by Macrogen USA. PCR amplification was accomplished with Qiagen's Hotstart Taq DNA polymerase and associated reagents (catalog no. 203205). The PCR primers for the three fragments are as follows: AHAS1F1 (forward primer at base pair 1-19 of the sunflower public sequence AY541451) 5'ATGGCGGCTCCTCCCAACC3'(SEQ ID NO:13), AHAS1R1 (reverse primer at base pair 757-777 of the sunflower public sequence AY541451) 5'CGGTAACCT-CATCGGTTCATC3' (SEQ ID NO:14), AHAS1F2 (forward primer at base pair 757-777 of the sunflower public sequence AY541451) 5'GATGAACCGATGAGGTTACCG3' (SEQ ID NO:15), AHAS1R2 (reverse primer at base pair 1794-1814 of the sunflower public sequence AY541451) 5'TCCGC-CTTTTGGGTCACTCGA3' (SEQ ID NO:16), AHAS1F3 (forward primer at base pair 1248-1269 of the sunflower public sequence AY541451) 5'GGTGACTAATCT-TGATTTTTCG3' (SEQ ID NO:17) and AHAS1R3 (reverse primer at base pair 1949-1968 of the sunflower public sequence AY541451) 5'TCAATATTTCGTTCTGCCAT3' (SEQ ID NO:18).

The three PCR fragments cover all the mutation sites known to confer resistance to the IMI herbicides. A nucleotide alignment was produced and the resulting chromatographs examined for polymorphisms between the susceptible line B770 and the resistant line RW-B.

Results from the Sequencing of Sunflower AHASL1 Gene

PCR products were sequenced to produce the AHASL1 sequences for RW-B and B770 sunflower lines. An alignment of these nucleotide sequences and the nucleotide sequences of the *Xanthium* sp. AHAS gene (Genbank Accession No U16280) is shown in FIG. 1.

In particular, FIG. 1 shows a partial DNA sequence alignment of the coding region of the AHASL1 gene from HA89 (GenBank acc. no. AY541451) (SEQ ID NO: 3), B770 line (SEQ ID NO: 4), resistant line RW-B (SEQ ID NO: 5), *Xanthium* sp. ALS gene (GenBank acc. no. U16280) (SEQ ID NO: 6) and *Arabidopsis thaliana* AHAS gene (GenBank acc. no. AY124092) (SEQ ID NO: 7). The asterisk points the single mutation found in RW-B, this base change is responsible for the Trp-to-Leu substitution in amino acidic position 574 (based on *Arabidopsis thaliana* sequence). Nucleotide sequence positions are indicated by arrows and are numbered according to *A. thaliana* sequence.

The alignment revealed that the AHASL1 gene from RW-B had a G-to-T transition relative to the AHASL1 of B770.

An alignment of the predicted amino acid sequences of the AHASL1 nucleotide sequences of RW-B, B770, and *Xanthium* sp is provided in FIG. 2.

In particular, FIG. 2 shows a partial amino acid sequence alignment of the AHASL1 protein from HA89 (GenBank acc. no. AY541451) (SEQ ID NO: 8), B770 line (SEQ ID NO: 9), resistant line RW-B (SEQ ID NO: 10), *Xanthium* sp. ALS gene (GenBank acc. no. U16280) (SEQ ID NO: 11) and *Arabidopsis thaliana* AHAS gene (GenBank acc. no. AY124092) (SEQ ID NO: 12). The asterisk points to the amino acid substitution in codon 574 (based on *Arabidopsis thaliana* sequence).

Relative to the AHASL1 amino acid sequence of B770, the AHASL1 amino acid sequence of RW-B has a tryptophan-to-leucine substitution at amino acid position 574 in the full-length amino acid sequence encoded by the *Arabidopsis thaliana* AHASL nucleotide sequence.

Comparison of Agronomic Characteristics (Grain Yield and Oil Content) of Sunflower Hybrids Carrying the 574 Event with Respect to Conventional (Wild Type) Hybrids and Those Carrying the 205 Event (IMISUN Trait).

Objective: This experiment was conducted to quantify and contrast the agronomic performance of hybrids carrying the 574 event with conventional (wild type) and imisun (event 205) hybrids. See Table 1

Materials: Line RW-B was converted to a male sterile line by repeated backcrossing with a cytoplasmic male sterile line (cms B770). After 4 backcrosses the obtained sterile line was named "cms RW-B".

Line RW-B was also used as a source of herbicide resistance to convert two different conventional (wild type) restorer lines: R20 and R54. The obtained near isogenic lines were designated R20-574 and R54-574.

F1 hybrids among conventional, IMISUN and RW-B derived lines were obtained under field conditions. The pedigree and mutation event of them are shown in the following Table.

TABLE 1

Hybrid 4 (cms B770 × R54) and Hybrid 6 (cms B770 × IR152) are two registered commercial hybrids known as "Paraíso 33" and "Paraíso 103 CL", respectively.

| Hybrid | Pedigree | Mutation event |
|---|---|---|
| 1 | cms RW-B × R20-574 | 574 |
| 2 | cms RW-B × R54-574 | 574 |
| 3 | cms B770 × R20 | wild type |
| 4 | cms B770 × R54 | wild type |
| 5 | cms B770 imi × IR79 | imisun |
| 6 | cms B770 imi × IR152 | imisun |

Methods: Seeds were sown under field conditions (Venado Tuerto, Santa Fe, Argentina) in a completely randomized block design with four replications. Each plot consisted in three rows 6 meters long and spaced 0.7 m. Seeds were spaced 0.30 m in the row.

The following variables were recorded in each plot: days to flowering, height at flowering, yield (kg/ha) and oil percent in the grain (%). An anova test was conducted over these variables and the means of the different events and hybrids were compared with the Tuckey test.

Results: Average values of each event for the 4 recorded variables are given in Table 2. As can be seen, the three events had similar average yields. The analysis detected differences for oil content in the seed among events, since the hybrids with the IMISUN event gave lower oil content than the other two types of hybrids. Days to flowering and Plant height were also different among events, since the hybrids carrying the 574 event were slightly smaller and earlier than the two other types of hybrids. In conclusion, the two hybrids carrying the event 574 showed the same yield and comparable oil content in the seed than the conventional (wild type) and the IMISUN hybrids, which included commercial hybrid varieties.

Means of each hybrid for each one of the recorded variables, and the results of the analysis of variance are given in Table 3.

TABLE 2

Average values for Height, Days to Flowering (DTF), Yield and Oil Content for 3 different genotypes (mutation events) for the AHASL1 locus. Average value of each genotype or mutation event is the mean value of two different hybrids.

| Event | Height (m) | DTF (days) | Yield (kg/ha) | Oil Content (%) |
|---|---|---|---|---|
| 574 | 2.14 $^{a1}$ | 63.3 $^a$ | 3062 $^a$ | 45.8 $^a$ |
| WT | 2.22 $^b$ | 66.4 $^b$ | 3523 $^a$ | 46.3 $^a$ |
| IMISUN | 2.17 $^{ab}$ | 65.8 $^b$ | 3119 $^a$ | 44.5 $^b$ |
| Mean | 2.18 | 65.1 | 3145 | 45.6 |
| $^1$CV(%) | 2.4 | 0.75 | 5.39 | 0.92 |
| $^2$MS | 0.015 | 21.9 | 76845 | 6.58 |
| F-value | 5.61 | 90.5 | 267 | 37.3 |
| $^3$p | <0.015 | <0.0001 | <0.101 | <0.0001 |
| $^4$MSD | 0.068 | 0.64 | 220.2 | 0.55 |

[1]Similar letters indicate that there are no statistically significant differences among events.
[2]CV: Coefficient of Variation
[3]MS: Mean Square among Events
[4]p: probability value of the F-value.
[5]MSD: Tuckey minimum significant difference

TABLE 3

Average values for Height, Days to Flowering (DTF), Yield and Oil Content for 6 sunflower hybrids carrying three different genotypes (mutation events) for the AHASL1 locus.

| Genotype | Mutation Event | Height (m) ± SD[1] | DTF (days) ± SD | Yield (kg/ha) ± SD | Oil Content (%) ± SD |
|---|---|---|---|---|---|
| Hib1 | W574L | 2.13 ± 0.05 [b] | 63.8 ± 0.5 [c] | 3053 ± 198 [a] | 45.48 ± 0.7 [bc] |
| Hib2 | W574L | 2.15 ± 0.06 [b] | 62.8 ± 0.5 [c] | 3071 ± 80 [a] | 46.18 ± 0.3 [ab] |
| Hib3 | WT | 2.28 ± 0.05 [a] | 66.3 ± 0.5 [ab] | 3370 ± 311 [a] | 47.13 ± 0.2 [a] |
| Hib4 | WT | 2.18 ± 0.05 [ab] | 66.5 ± 0.5 [a] | 3135 ± 249 [a] | 45.45 ± 0.4 [bc] |
| Hib5 | A205V | 2.20 ± 0 [ab] | 65.3 ± 0.5 [b] | 3059 ± 145 [a] | 44.80 ± 0.2 [cd] |
| Hib6 | A205V | 2.15 ± 0.06 [b] | 66.3 ± 0.5 [ab] | 3179 ± 164 [a] | 44.28 ± 0.3 [d] |
| Mean | | 2.18 | 65.13 | 3144 | 45.6 |
| [2]CV(%) | | 2.4 | 6.75 | 5.4 | 0.92 |
| [3]MS | | 0.00042 | 9.58 | 58798.7 | 4.06 |
| F-value | | 0.15 | 39.6 | 2.05 | 23.04 |
| [4]p | | 0.014 | 0.0001 | 0.13 | 0.0001 |
| [5]MSD | | 0.12 | 1.13 | 389.6 | 0.96 |

[1]SD: Standard Deviation, followed by a letter which indicates if there exist differences among hybrids: similar letters indicate that there are no statistically significant differences.
[2]CV: Coefficient of Variation
[3]MS: Mean Square among Hybrids
[4]p: probability value of the F-value.
[5]MSD: Tuckey minimum significant difference.

Tolerance of RW-B to 4 Different Mixes of Two AHAS-Inhibitor Herbicides.

Objective: to compare the performance (evaluated as Phytotoxicity index) of a line carrying the 574 event (RW-B) and lines carrying the SURES, IMISUN, and wild type events.

Materials: The following sunflower inbred lines were used: two imidazolinone susceptible lines ("B770" and "HA89"), two lines resistant to SUs herbicides derived from SURES population ("SuBL" and "SuRL"), two lines resistant to IMIs herbicides derived from IMISUN ("RHA426" and "B770imi") and the line "RW-B", which carries the event 574. HA89 and RHA426 are public inbred lines released by the USDA. B770 and B770imi are proprietary lines from Nidera S.A., while B770imi have a B770 genetic background carrying the resistance gene Imr1 for resistance to imidazolinones. RW-B was obtained as described above.

Method: Eight seeds from each of the seven lines were sown in 20-by-20-by-30 cm pots. After emergence, plantlets were thinned by hand leaving 4 plantlets per pot. Five pots of each line were treated with a different mix of herbicides. An untreated control pot of each line was included in each experiment. Plants were grown in a greenhouse under natural light conditions supplemented with 400 W halide lamps to provide a 14 h day length. Day/night temperatures were 25 and 20° C., respectively. At V4 stage of development (Schneiter and Miller 1981) plants were sprayed with four different mixes containing two different AHAS-inhibiting herbicides, a sulfonuylurea (Metsulfuron) and an imidazolinone (Imazapyr). Herbicide concentrations of each one of the four herbicide mixes were as follows: Mix A was 20 g a.i./ha imazapyr and 1.25 g a.i./ha metsulfuron, Mix B was 40 g a.i./ha imazapyr and 2.5 g a.i./ha metsulfuron, Mix C was 80 g a.i./ha imazapyr and 5 g a.i./ha metsulfuron and Mix D was 160 g a.i./ha imazapyr and 10 g a.i./ha metsulfuron.

Fourteen days after treatment plants were scored phenotypically using a Phytotoxicity Index (PI). PI is a phenotypic scale from 0 to 9 that was assessed for each pot by visual inspection. Plants without any symptoms were recorded as "0," increasing levels of stunting and yellowing with respect to the untreated control plants were recorded as "1" to "4," increasing levels of leaf abnormalities and leaf necrosis were recorded from "5" to "8," and dead plants with total necrosis of the apex were recorded as "9." PI data for each experiment were analyzed by an ANOVA test; means were compared by a Tuckey test.

The results are shown in Table 4. Lines HA89 and B770 were killed by all herbicide mix applications. The SU-resistant lines SuBL and SuRL showed some level of tolerance to Mix A and Mix B, but reached a high level of leaf necrosis and stunting as the doses of herbicides increases, for example with the Mix C. All plants were killed with the Mix D, which had the highest doses of active ingredients. The IMI-resistant lines RHA426 and B770imi were moderately resistant to Mix A, Mix B, and Mix C, even though they showed an increased damage as the dose of herbicides increased. When Mix D was applied to these lines, all plants were killed. Remarkably, RW-B, showed tolerance to all of the mixes tested, even at the mix which had the highest concentration of active ingredients.

Conclusion: RW-B shows not only a higher level of tolerance to each one of the AHAS inhibitor herbicides tested alone but also, the highest level of tolerance to a combination of herbicides tested simultaneously in a mix.

TABLE 4

Average Phytotoxicity Index of 7 sunflower lines carrying different mutation events at the locus AHASL1 when challenged to 4 mixes of two AHAS inhibitor herbicides.

| | | | Herbicide Mix | | | |
|---|---|---|---|---|---|---|
| | | | A | B | C | D |
| | AHAS1 | imazapyr (g a.i. ha$^{-1}$) | 20 | 40 | 80 | 160 |
| Genotype | Mutation | metsulfuron (g a.i. ha$^{-1}$) | 1.25 | 2.5 | 5 | 10 |
| B770 | WT | | 9[a] | 9[a] | 9[a] | 9[a] |
| Ha89 | WT | | 9[a] | 9[a] | 9[a] | 9[a] |
| SuBL | P197L | | 0.8[c] | 3[cd] | 8.4[a] | 9[a] |
| SuRL | P197L | | 2.2[b] | 4.4[b] | 8.4[a] | 9[a] |
| B770imi | A205V | | 1.2[c] | 2.2 | 4.4[c] | 8.8[a] |
| Rha426 | A205V | | 0.8[c] | 3.4[c] | 5.4[b] | 9[a] |
| RW-B | W574L | | 0[d] | 0[e] | 0.2[d] | 0.8[b] |
| Mean | | | 3.3 | 4.4 | 6.4 | 7.8 |
| MS[1] | | | 47.1 | 34.8 | 32.5 | 28.6 |

TABLE 4-continued

Average Phytotoxicity Index of 7 sunflower lines carrying different mutation events at the locus AHASL1 when challenged to 4 mixes of two AHAS inhibitor herbicides.

| | Herbicide Mix | | | |
|---|---|---|---|---|
| | A | B | C | D |
| p[2] | <0.0001 | <0.0001 | <0.0001 | <0.0001 |
| MSD[3] | 0.634 | 0.835 | 0.919 | 0.495 |

[1]MS: Mean Square
[2]p: probability
[3]MSD: Minimum significant difference

Response of Homozygous W574L Mutation Compared with Homozygous A205V and P197L Mutations and the Susceptible Haplotype to Imazapyr at the Whole Plant Level.

Objective: This experiment was conducted to quantify and contrast the imazapyr sensitivity of sunflower lines carrying the homozygous W574L mutation compared with homozygous P197L and A205V at the whole plant level. See Table 5.

Materials:

TABLE 5 shows seeds of the different sunflower lines, which were obtained under field conditions.

| Code | Mutation Event |
|---|---|
| B770 | WT-Susceptible |
| B770IMI | A205V |
| SuBL | P197L |
| RW-B | W574L |

Seeds were sown in Petri dishes and, after germination; plantlets were transplanted to pots of 10 cm of diameter in a potting media consisting of equal parts of vermiculite, soil and sand. Plants were grown in a greenhouse under natural light conditions supplemented with 400 W sodium halide lamps to provide a 16 hr day-length. Day/night temperatures were 25 and 20° C., respectively. At the V2-V4 stage (Schneiter & Miller, 1981) 10 plants of each genotype were randomly assigned to each treatment consisting of eight imazapyr doses (0, 40, 80, 160, 320, 480, 640 and 800 g ai/ha, without treatment, 0.5×, 1×, 2×, 4×, 6×, 8× and 10× respectively), and a zero-time biomass determination. Experiment was arranged as a randomized block design with a full factorial (sunflower line x treatment) arrangement of treatments and 10 replications.

On the day of herbicide application ten plants of each genotype were cut at the cotyledonal node and dried at 60° C. for 48 hrs for zero-time dried weight determination.

The remaining plants were maintained for 14 days after imazapyr treatment (DAT) and their height, Phytotoxicity Index (PI) and above ground dry biomass were determined. Height was determined as the distance between the cotyledonal node and the apex of each plant. Above ground biomass data from each line were converted to biomass accumulation after application by subtracting the appropriate average zero-time biomass from each sample. Dry biomass data were converted to percentages of the untreated control plants within each line to allow direct comparisons between groups. PI is a phenotypic scale from 0 to 9 that was assessed for each plant by visual inspection. Plants without any symptoms were recorded as "0", increasing levels of stunting and chlorosis with respect to the untreated control plants were recorded as "1" to "4", increasing levels of leaf abnormalities and leaf necrosis were recorded from "5" to "8", and dead plants with total necrosis of the apex were recorded as "9".

Results: Height. After imidazolinone application plant height was severely reduced in susceptible (B770) and SU tolerant (SuBL) lines. In fact, even at the lower rate of herbicide spraying (0.5×), height was reduced from 100% in the untreated control plants to 35.0% and 42.7% in the susceptible and the SU tolerant lines, respectively. The IMI tolerant line (B770IMI) showed a significant reduction in height only after the 2× rate of herbicide application, and then, as the herbicide rate increased height reduction was greater, approaching the same level of the susceptible line at 10× (32.8%).

In contrast, sunflower line RW-B exhibited a smaller height reduction when challenged to increased doses of imidazolinones. This reduction in height reached only 75% of the untreated control plants from 4× to 10× rates of herbicide application. (Table 6 and FIG. 9).

TABLE 6

Height reduction (as percentage of the untreated control plants) for 4 lines carrying different mutant alleles at the AHASL1 locus of sunflower when challenged with increased rates of imazapyr.
Height (as % of the untreated plants)

| | Dose (x) | | | | | | | |
|---|---|---|---|---|---|---|---|---|
| | 0 | 0.5 | 1 | 2 | 4 | 6 | 8 | 10 |
| SuBL | 100 | 42.7[b] | 39.1[b] | 37.2[c] | 37.0[c] | 36.1[c] | 35.5[c] | 35.1[b] |
| B770IMI | 100 | 97.7[a] | 95.2[a] | 70.2[b] | 64.0[b] | 51.9[b] | 40.7[b] | 32.8[c] |
| B770 | 100 | 35.0[c] | 31.8[c] | 31.9[d] | 31.9[d] | 31.6[d] | 31.7[d] | 31.4[c] |
| RW-B | 100 | 98.0[a] | 95.4[a] | 85.7[a] | 75.6[a] | 73.9[a] | 73.9[a] | 73.4[a] |
| Mean | | 68.3 | 65.4 | 56.2 | 52.1 | 48.4 | 45.4 | 43.2 |
| MS[1] | | 2926.8 | 3008.3 | 1682.6 | 1109.8 | 913.7 | 934.1 | 1022.3 |
| p[2] | | <0.0001 | <0.0001 | <0.0001 | <0.0001 | <0.0001 | <0.0001 | <0.0001 |
| MSD[3] | | 1.27 | 1.287 | 1.159 | 1.216 | 1.129 | 1.294 | 1.558 |

[1]MS: Mean Square
[2]p: probability
[3]MSD: Minimum significant difference

Phytotoxicity Index

The mutants showed great differences in their symptoms after the application of increased rates of imazapyr. Sunflower line RW-B showed only a slight reduction in leaf size and lighter green color that the control plants as the herbicide rates increased (Table 7). In contrast, even though plants carrying the A205V mutation (B770IMI) did not showed any injury at 0.5× rate, they presented an increased level of injury (chlorosis, leaf deformation and leaf necrosis) as the doses of imazapyr increased from 1× to 10×. Su-tolerant and susceptible lines showed an almost identical behavior: a total susceptibility from 0.5× to 10× rates of herbicide application.

ing the homozygous W574L mutation compared with homozygous P197L and A205V at the whole plant level. See Table 9.

TABLE 7

Phytotoxicity Index for 4 sunflower lines carrying different mutant alleles at the AHASL1 locus of sunflower when challenged with increased rates of imazapyr.

| | Dose (x) | | | | | | | |
|---|---|---|---|---|---|---|---|---|
| | 0 | 0.5 | 1 | 2 | 4 | 6 | 8 | 10 |
| B770 | 0 | 8.9$^a$ | 9$^a$ | 9$^a$ | 9$^a$ | 9$^a$ | 9$^a$ | 9$^a$ |
| SuBL | 0 | 8.6$^a$ | 9$^a$ | 9$^a$ | 9$^a$ | 9$^a$ | 9$^a$ | 9$^a$ |
| B770IMI | 0 | 0.2$^b$ | 1.7$^b$ | 4.5$^b$ | 4.9$^b$ | 5.8$^b$ | 6.8$^b$ | 7$^b$ |
| RW-B | 0 | 0$^b$ | 0.1$^c$ | 0.7$^c$ | 0.9$^c$ | 1.5$^c$ | 2.3$^c$ | 2.4$^c$ |
| Mean | | 4.4 | 4.9 | 5.8 | 5.9 | 6.3 | 6.8 | 6.8 |
| MS$^1$ | | 62.5 | 55.9 | 40.3 | 37.8 | 31.6 | 25.0 | 24.3 |
| p$^2$ | | <0.0001 | <0.0001 | <0.0001 | <0.0001 | <0.0001 | <0.0001 | <0.0001 |
| MSD$^3$ | | 0.464 | 0.605 | 0.421 | 0.365 | 0.445 | 0.498 | 0.428 |

$^1$MS: Mean Square
$^2$p: probability
$^3$MSD: Minimum significant difference

Above Ground Dry Weight Biomass

Dose response curves for dry weight of mutants W574L, P197L and 205V are shown in FIG. 11. Biomass dry weight of event W574L in homozygous condition was reduced with respect to the untreated control plants only at 6×, 8× and 10× rates of herbicide application. Dry weight of RW-B plants at 10× rate was 78% of the untreated controls. Meanwhile, dry weight of all the other mutants and wild type line differed significantly from those of the line RW-B at each one of the doses tested (Table 8).

Materials:

TABLE 9 shows the seeds of the different sunflower lines, which were obtained under field conditions

| Code | Mutation Event |
|---|---|
| B770 | WT-Susceptible |
| B770IMI | A205V |
| SuBL | P197L |
| RW-B | W574L |

TABLE 8

Above ground dry weight biomass (as percentage of the untreated control plants) for 4 sunflower lines carrying different mutant alleles at the AHASL1 locus of sunflower when challenged with increased rates of imazapyr.
Dry weight (as a % of the untreated plants)

| | Dose (x) | | | | | | | |
|---|---|---|---|---|---|---|---|---|
| | 0 | 0.5 | 1 | 2 | 4 | 6 | 8 | 10 |
| SuBL | 100 | 46.6$^c$ | 41.3$^c$ | 38.9$^c$ | 38.0$^c$ | 37.8$^c$ | 37.4$^c$ | 36.4$^c$ |
| B770IMI | 100 | 96.2$^b$ | 88.5$^b$ | 73.7$^b$ | 69.0$^b$ | 62.5$^b$ | 52.1$^b$ | 42.2$^b$ |
| B770 | 100 | 32.7$^d$ | 30.2$^d$ | 27.6$^d$ | 26.5$^d$ | 25.9$^d$ | 25.7$^d$ | 25.2$^d$ |
| RW-B | 100 | 99.1$^a$ | 97.9$^a$ | 97.0$^a$ | 92.1$^a$ | 85.1$^a$ | 80.2$^a$ | 78.2$^a$ |
| Mean | | 68.6 | 64.5 | 59.3 | 56.4 | 52.8 | 48.8 | 45.5 |
| MS$^1$ | | 2888.5 | 2839.5 | 2542.4 | 2222.2 | 1738.9 | 1384.3 | 1312.9 |
| p$^2$ | | <0.0001 | <0.0001 | <0.0001 | <0.0001 | <0.0001 | <0.0001 | <0.0001 |
| MSD$^3$ | | 1.127 | 1.009 | 1.480 | 1.137 | 1.076 | 0.846 | 1.377 |

$^1$MS: Mean Square
$^2$p: probability
$^3$MSD: Minimum significant difference

Conclusion: line RW-B, which carries the mutant event W574L in homozygous condition at the AHASL1 locus of sunflower, presented a greater level of tolerance to all the tested doses of imazapyr than the Su-tolerant and the already known IMI tolerant lines.

Response of W574L Mutation Compared with A205V and P197L Mutations and the Susceptible Haplotype to Metsulfuron at the Whole Plant Level.

Objective: This experiment was conducted to quantify and contrast the metsulfuron sensitivity of sunflower lines carry- Seeds were sown in Petri dishes and, after germination, plantlets were transplanted to pots of 10 cm of diameter in a potting media consisting of equal parts of vermiculite, soil and sand. Plants were grown in a greenhouse under natural light conditions supplemented with 400 W sodium halide lamps to provide a 16 hr daylight. Day/night temperatures were 25 and 20° C., respectively. At the V2-V4 stage (Schneiter & Miller, 1981 . . . ) 10 plants of each genotype were randomly assigned to each treatment consisting of eight imazapyr doses (0, 2.5, 5, 10, 15, 20 g ai/ha, without treatment, 0.5×, 1×, 2×, 3×, and 4× respectively), and a zero-time biomass determination. Experiment was arranged as a randomized block design with a full factorial (sunflower line x treatment) arrangement of treatments and 10 replications.

On the day of herbicide application ten plants of each genotype were cut at the cotyledonal node and dried at 60° C. for 48 hrs for zero-time dried weight determination.

The remaining plants were maintained for 14 days after imazapyr treatment (DAT) and their Phytotoxicity Index (PI) and above ground dry biomass were determined. Above ground biomass data from each line were converted to biomass accumulation after application by subtracting the appropriate average zero-time biomass from each sample. Dry biomass data were converted to percentages of the untreated control plants within each line to allow direct comparisons between groups. PI is a phenotypic scale from 0 to 9 that was assessed for each plant by visual inspection. Plants without any symptoms were recorded as "0", increasing levels of stunting and chlorosis with respect to the untreated control plants were recorded as "1" to "4", increasing levels of leaf abnormalities and leaf necrosis were recorded from "5" to "8", and dead plants with total necrosis of the apex were recorded as "9".

Results, Phytotoxicity Index: Mutants showed great differences in their response to increased rates of metsulfuron application (Table 10 and FIG. 12). The conventional genotype (B770) was killed even at the lower doses of metsulfuron. Sunflower line carrying W574L mutation in homozygous conditions showed only a slight reduction in plant size and lighter green color that the control plants as the herbicide rates increased from 0.5 to 3× (Table 10). In fact, it only showed chlorosis and deformations when 4× rate of metsulfuron was applied. In contrast, the line carrying the A205V mutation (B770IMI) showed an increased level of injury from 0.5× to 4× rate. In fact, at 2× rate of metsulfuron application, almost all the plants of this line were killed by the herbicide.

SU-tolerant line (SuBL), which carries the already known mutant allele for sulfonylurea tolerance in sunflower, showed no symptoms or a slight chlorosis at 0.5× and 1× doses of metsulfuron application, but then its injury level increased, reaching a score of 9 (all the plants were killed by the herbicide) at 4× rate of metsulfuron.

TABLE 10

Phytotoxicity Index for 4 sunflower lines carrying different mutant alleles at the AHASL1 locus of sunflower when challenged with increased rates of metsulfuron.

| | Dose (x) | | | | | |
|---|---|---|---|---|---|---|
| | 0 | 0.5 | 1 | 2 | 3 | 4 |
| B770 | 0 | $9^a$ | $9^a$ | $9^a$ | $9^a$ | $9^a$ |
| SuBL | 0 | $0.1^c$ | $1.7^c$ | $4.3^c$ | $7.2^b$ | $9^a$ |
| B770IMI | 0 | $3.3^b$ | $5.2^b$ | $8.5^b$ | $9^a$ | $9^a$ |
| RW-B | 0 | $0^c$ | $0.6^d$ | $1.1^d$ | $2.8^c$ | $5.6^b$ |
| Mean | | 3.10 | 4.13 | 5.73 | 7.00 | 8.15 |
| MS[1] | | 178.2 | 144.1 | 139.5 | 85.6 | 28.9 |
| p[2] | | <0.001 | <0.001 | <0.001 | <0.001 | <0.001 |
| MSD[3] | | 0.325 | 0.498 | .430 | 0.387 | 0.316 |

[1]MS: Mean Square
[2]p: probability
[3]MSD: Minimum significant difference

Results, Above ground dry weight biomass: Dose response curves for dry weight of mutants W574L, P197L and 205V are shown in FIG. 5 and Table 11. IMI tolerant and susceptible lines showed an immediate reduction in dry weight after herbicide application. Biomass of the SU-tolerant line was reduced from 83.3% to 30.3% of the untreated control plants as metsulfuron rates increased from 0.5 to 4×.

Interestingly, RW-B line did not show a significant reduction in dry weight at 0.5 and 1× rate of metsulfuron application. As the doses increased, a significant reduction of dry weight was observed. However, this line showed significantly higher dry weight than any of the other lines at each one of the doses tested.

TABLE 11

Above ground dry weight biomass (as percentage of the untreated control plants) for 4 sunflower lines carrying different mutant alleles at the AHASL1 locus of sunflower when challenged with increased rates of metsulfuron.
Dry weight (as a % of the untreated plants)

| | Dose (x) | | | | | |
|---|---|---|---|---|---|---|
| | 0 | 0.5 | 1 | 2 | 3 | 4 |
| SuBL | 100 | $83.3^b$ | $72.4^b$ | $52.2^b$ | $35.7^b$ | $30.3^b$ |
| B770IMI | 100 | $42^c$ | $30.1^c$ | $30.4^c$ | $30^c$ | $30.2^b$ |
| Suscp | 100 | $23.7^d$ | $20^d$ | $19.4^d$ | $19.2^d$ | $19.4^c$ |
| RW-B | 100 | $94.6^a$ | $90.4^a$ | $73.9^a$ | $60.7^a$ | $38.1^a$ |
| Mean | | 60.9 | 53.2 | 44.2 | 36.4 | 29.5 |
| MS[1] | | 11261.7 | 11294.4 | 5895.2 | 3092.6 | 590.3 |
| p[2] | | <0.001 | <0.001 | <0.001 | <0.001 | <0.001 |
| MSD[3] | | 2.998 | 2.099 | 2.07 | 1.630 | 1.992 |

[1]MS: Mean Square
[2]p: probability
[3]MSD: Minimum significant difference

Conclusion: line RW-B, which carries the mutant event W574L in homozygous condition at the AHASL1 locus of sunflower, presented a greater level of tolerance to all the tested doses of metsulfuron than the IMI-tolerant and the already known SU-tolerant lines.

The Morphological and Physiological Characteristics of Cultivar RW-B

The seed from the deposited cultivar known as RW-B is true breeding for the morphological traits of producing a plant with a single head, combined resistance to the 4 herbicide families and mixtures thereof, a yield of greater than one tonne per hectare and for producing a seed having an oil content of greater than 40%. See Table 12 for additional physiological and morphological RW-B line. More particularly, in terms of resistance, the specification teaches (i) resistance to cloransulam-methyl present in a concentration of at least 67 grams of active ingredient per hectare; and (ii) resistance to the mix of imazapyr present in a concentration of at least 160 grams per hectare and metsulfuron present in a concentration of at least 10 grams per hectare.

In addition, as shown in Table 8, the sunflower plants having the W574L mutation (RW-B) are significantly more robust and have significantly less height reduction (e.g., 73.4% remaining v. 32.8% remaining at 10× dose) than those sunflower plants bearing the A205V mutation (B770IMI).

Table 10 shows the phytotoxicity index, which measures the level of injury of the plants. As shown in Table 11, an increased level of injury (chlorosis, leaf deformation and leaf necrosis) is observed for B770IMI as compared to RW-B (e.g., 7 v. 2.4 at 10× dose).

As shown in Table 11, the ground dry weight biomass of RW-B is significantly greater than that of B770IMI (e.g., 78.2 remaining v. 42.2% remaining at 10× dose).

Plant having the W574L mutation shows not only a higher level of tolerance to each one of the AHAS inhibitor herbicides tested alone, but also, the highest level of tolerance to a combination of herbicides tested simultaneously in a mix. In an experiment, Applicant measured the level of injury to sunflower plants after treatment with four different mixes containing different doses of two different AHAS inhibitor herbicides, a sulfonylurea and an imidazolinole. As shown in Table 4, the sunflower plants carrying the A205V or P197L mutations had significantly higher injury than the sunflower plants carrying the W574L mutation. For example, for herbicide mix B which contains 40 g a.i./ha imazapyr and 2.5 g a.i./ha metsulfuron, the injury index was zero in sunflower plants carrying the W574L mutation. In contrast, the injury index was 3.5 in sunflower plants carrying the P197L mutation. Therefore, the W574L mutation of RW-B confers a surprising and unexpected advantageous resistance to mixtures of herbicides.

TABLE 12

Physiologial and morphological features of RW-B line.

| Feature | Stage/organ | Value | Observations |
|---|---|---|---|
| hypocothyl anthocianyc pigmentation | plantlet | medium | |
| mean height (cm) | plant | 135 | reference line HA89:110 cm |
| stem diameter (cm) | plant | 2.4 | at physiological maturity (R9). Measured at the first internode height at a plant density of 40000-45000 plants per hectare |
| stem epidermal hair | plant | medium | Measured at 5 cm below the head during flowering |
| leaf shape | plant | cordate | during flowering in the upper third part of the plant |
| colour | leaf | dark green | |
| number of leaves | plant | 29 | |
| leaf lay length (cm) | plant | 23 | |
| width lay length (cm) | leaf | 22 | |
| petiole length (cm) | leaf | 12 | |
| leaf lay surface | leaf | medium roughly | |
| leaf margin serrate | leaf | strong | |
| head diameter (cm) | capitulum | 18 | measured at maturity |
| receptacule width | capitulum | medium | measured at flowering |
| ray floret colour | capitulum | yellow-golden | measured at flowering |
| disk florets | capitulum | orange | measured at flowering |
| anthers colour | capitulum | brown | measured at flowering |
| pollen grain colour | capitulum | yellow | measured at flowering |
| stigmas anthocianins | capitulum | absent | measured at flowering |
| main pericarp colour | seed | black | |
| stripes | seed | present | |
| motled | seed | absent | |
| days to flowering | plant | 69 | reference line HA89:67. Measured at 50 % of anthesis |
| resistance to Plasmopara halstedii (race 770) | plant | resistant | artificial inoculation |
| resistance to Puccinia helianthi (race 710) | plant | susceptible | artificial inoculation |

What is claimed is:

1. A seed of sunflower cultivar designated RW-B, a representative seed of said sunflower cultivar was deposited under ATCC Accession No: PTA-9176.

2. A sunflower plant, or a part thereof, produced by growing the seed of claim 1.

3. Pollen of the plant of claim 2.

4. An ovule of the plant of claim 2.

5. A sunflower plant, or part thereof, having all the characteristics of the plant according to claim 2.

6. A seed of the plant of claim 5.

7. A tissue culture of regenerable cells of the sunflower plant according to claim 2.

8. The tissue culture according to claim 7, wherein the cells of the tissue culture comprise a leaf, pollen, an embryo, a cotyledon, a hypocotyl, meristematic cells, a root, a root tip, an anther, a flower, a seed, a stem, ovules, shoots, stems, stalks, pith capsules or a pod.

9. A sunflower plant generated from the tissue culture of claim 8, wherein the regenerated plant expresses all the morphological and physiological characteristics of sunflower cultivar RW B.

10. A method for producing a sunflower seed, comprising
crossing a first parent sunflower plant with a second parent sunflower plant, and
harvesting the resultant first generation sunflower seed, wherein the first or second parent sunflower plant is a sunflower plant selected from the group consisting of the sunflower plant of claim 2 and claim 5, and a sunflower plant derived from the sunflower plant of claim 2 or 5; and
determining whether the seed produces a plant expresses all the morphological and- physiological characteristics of sunflower cultivar RW-B.

11. A method for producing a RW-B-derived sunflower plant, comprising:
crossing the sunflower line RW-B, representative seed of the sunflower cultivar RW-B having been deposited under ATCC Accession No. PTA-9176, with a second sunflower plant to yield a progeny sunflower seed;
growing the progeny sunflower seed to yield the RW-B-derived sunflower plant and;
determining whether the progeny sunflower seed produces a plant expressing all the morphological and physiological characteristics of sunflower cultivar RW-B.

12. A tissue culture of regenerable cells of the sunflower plant according to claim 5.

13. The tissue culture according to claim 12, wherein the cells of the tissue culture are from a leaf, pollen, an embryo, a cotyledon, a hypocotyl, meristematic cells, a root, a root tip, an anther, a flower, a seed, a stem, ovules, shoots, stems, stalks, pith capsules or a pod.

14. A sunflower plant generated from the tissue culture of claim 12, wherein the sunflower plant expresses all the morphological and physiological characteristics of sunflower cultivar RW-B.

15. A sunflower plant obtained from a seed produced by the method of claim 10, wherein the sunflower plant expresses all the morphological and physiological characteristics of sunflower cultivar RW-B.

16. A sunflower plant seed obtained from a plant produced by the method of claim 11, wherein the sunflower plant expresses all the morphological and- physiological characteristics of sunflower cultivar RW-B.

* * * * *

UNITED STATES PATENT AND TRADEMARK OFFICE
CERTIFICATE OF CORRECTION

| | | |
|---|---|---|
| PATENT NO. | : 8,952,222 B2 | Page 1 of 1 |
| APPLICATION NO. | : 13/056237 | |
| DATED | : February 10, 2015 | |
| INVENTOR(S) | : Carlos Sala and Mariano Bulos | |

It is certified that error appears in the above-identified patent and that said Letters Patent is hereby corrected as shown below:

In the Claims

Col. 55 in claim 10, line 11, please correct a typography as follows:
Delete the "-" after "and".

Col. 56 in claim 16, line 3, please correct a typography as follows:
Delete the "-" after "and".

Signed and Sealed this
Twenty-sixth Day of May, 2015

Michelle K. Lee
*Director of the United States Patent and Trademark Office*